United States Patent
Schings

(10) Patent No.: US 12,364,476 B2
(45) Date of Patent: *Jul. 22, 2025

(54) PIN TRAP MECHANISM FOR SURGICAL LINEAR CUTTER

(71) Applicant: Cilag GmbH International, Zug (CH)

(72) Inventor: Brian D. Schings, Maineville, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/612,395

(22) Filed: Mar. 21, 2024

(65) Prior Publication Data
US 2024/0225643 A1 Jul. 11, 2024

Related U.S. Application Data

(63) Continuation of application No. 17/569,050, filed on Jan. 5, 2022, now Pat. No. 11,957,340, which is a
(Continued)

(51) Int. Cl.
*A61B 17/072* (2006.01)
*A61B 17/11* (2006.01)
(Continued)

(52) U.S. Cl.
CPC ...... *A61B 17/072* (2013.01); *A61B 17/07207* (2013.01); *A61B 17/1114* (2013.01);
(Continued)

(58) Field of Classification Search
CPC ............... A61B 17/068; A61B 17/072; A61B 17/07207; A61B 17/115;
(Continued)

(56) References Cited

U.S. PATENT DOCUMENTS

| | | |
|---|---|---|
| 4,608,981 A | 9/1986 | Rothfuss et al. |
| 5,718,359 A | 2/1998 | Palmer et al. |

(Continued)

FOREIGN PATENT DOCUMENTS

| | | |
|---|---|---|
| CN | 103654900 A | 3/2014 |
| EP | 2532313 A2 | 12/2012 |
| EP | 3085314 A1 | 10/2016 |

OTHER PUBLICATIONS

International Search Report and Written Opinion dated Nov. 23, 2021, for International Application No. PCT/EP2021/064434, 23 pages.
(Continued)

*Primary Examiner* — Scott A Smith
(74) *Attorney, Agent, or Firm* — Frost Brown Todd LLP

(57) ABSTRACT

A surgical stapler includes a first stapler half including an anvil surface having a plurality of staple forming pockets, and a second stapler half configured to releasably couple with the first stapler half. The second stapler half is operable to deploy staples toward the anvil surface. The stapler also includes a projection positioned on one of the stapler halves and extending laterally relative to a longitudinal axis of the stapler. The stapler halves are configured to pivot relative to each other about the projection. The stapler further includes a locking member positioned on the other of the stapler halves. The locking member is configured to translate along the longitudinal axis of the stapler between a locked state in which the locking member selectively captures the projection and an unlocked state in which the locking member selectively releases the projection. The locking member is biased proximally toward the locked state.

20 Claims, 22 Drawing Sheets

Related U.S. Application Data continuation of application No. 16/886,920, filed on May 29, 2020, now Pat. No. 11,219,454.

(51) Int. Cl.
  *A61B 17/115* (2006.01)
  *A61B 17/00* (2006.01)
  *A61B 17/068* (2006.01)
  *A61B 17/29* (2006.01)

(52) U.S. Cl.
  CPC ... *A61B 17/115* (2013.01); *A61B 2017/00367* (2013.01); *A61B 2017/00477* (2013.01); *A61B 17/068* (2013.01); *A61B 2017/07214* (2013.01); *A61B 2017/07264* (2013.01); *A61B 2017/07271* (2013.01); *A61B 2017/07285* (2013.01); *A61B 2017/2927* (2013.01); *A61B 2017/2946* (2013.01)

(58) Field of Classification Search
  CPC .......... A61B 2017/00473; A61B 2017/00477; A61B 2017/07214; A61B 2017/07271; A61B 2017/07285; A61B 2017/2927; A61B 2017/2946
  USPC ............. 227/19, 175.2, 175.3, 176.1, 180.1; 606/1, 139, 219
  See application file for complete search history.

(56) References Cited

U.S. PATENT DOCUMENTS

| | | | |
|---|---|---|---|
| 5,878,938 | A | 3/1999 | Bittner et al. |
| 7,334,717 | B2 | 2/2008 | Rethy et al. |
| 7,832,612 | B2 | 11/2010 | Baxter, III et al. |
| 8,505,801 | B2 | 8/2013 | Ehrenfels et al. |
| 9,402,629 | B2 | 8/2016 | Ehrenfels et al. |
| 10,631,866 | B2 | 4/2020 | Laurent et al. |
| 10,898,187 | B2 | 1/2021 | Deck et al. |
| 11,219,454 | B2 | 1/2022 | Schings et al. |
| 11,224,425 | B2 | 1/2022 | Schings |
| 11,399,827 | B2 | 8/2022 | Schings |
| 11,439,398 | B2 * | 9/2022 | Laurent ............... A61B 17/1114 |
| 11,896,218 | B2 * | 2/2024 | Bakos ............. A61B 17/07207 |
| 11,957,340 | B2 | 4/2024 | Schings et al. |
| 2010/0072253 | A1 | 3/2010 | Baxter, III et al. |
| 2012/0024936 | A1 | 2/2012 | Baxter, III et al. |
| 2016/0249920 | A1 | 9/2016 | Gupta et al. |
| 2019/0239882 | A1 | 8/2019 | McLain et al. |
| 2019/0239883 | A1 | 8/2019 | Baxter, III et al. |
| 2019/0239884 | A1 | 8/2019 | Baxter, III et al. |
| 2019/0239885 | A1 | 8/2019 | Stokes et al. |
| 2019/0239886 | A1 | 8/2019 | Jones et al. |
| 2020/0046350 | A1 | 2/2020 | Deck et al. |
| 2020/0046351 | A1 | 2/2020 | Jones et al. |
| 2020/0046353 | A1 | 2/2020 | Deck et al. |
| 2020/0113561 | A1 | 4/2020 | Schings et al. |
| 2020/0113562 | A1 | 4/2020 | Schings et al. |
| 2021/0038223 | A1 | 2/2021 | Schings et al. |
| 2021/0369271 | A1 | 12/2021 | Schings et al. |

OTHER PUBLICATIONS

Japanese First Office Action dated Dec. 3, 2024, for Application No. 2022-573263, 4 pages.
U.S. Pat. No. 11,219,454.
U.S. Pat. No. 11,957,340.
Chinese First Office Action and Search Report dated Apr. 14, 2025, for Application No. 202180039059.X, 20 pages.

* cited by examiner

PIN TRAP MECHANISM FOR SURGICAL LINEAR CUTTER

PRIORITY

This application is a continuation of U.S. patent application Ser. No. 17/569,050, entitled "Pin Trap Mechanism for Surgical Linear Cutter," filed Jan. 5, 2022, issued as U.S. Pat. No. 11,957,340 on Apr. 16, 2024, which is a continuation of U.S. patent application Ser. No. 16/886,920, entitled "Pin Trap Mechanism for Surgical Linear Cutter," filed May 29, 2020, issued as U.S. Pat. No. 11,219,454 on Jan. 11, 2022.

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
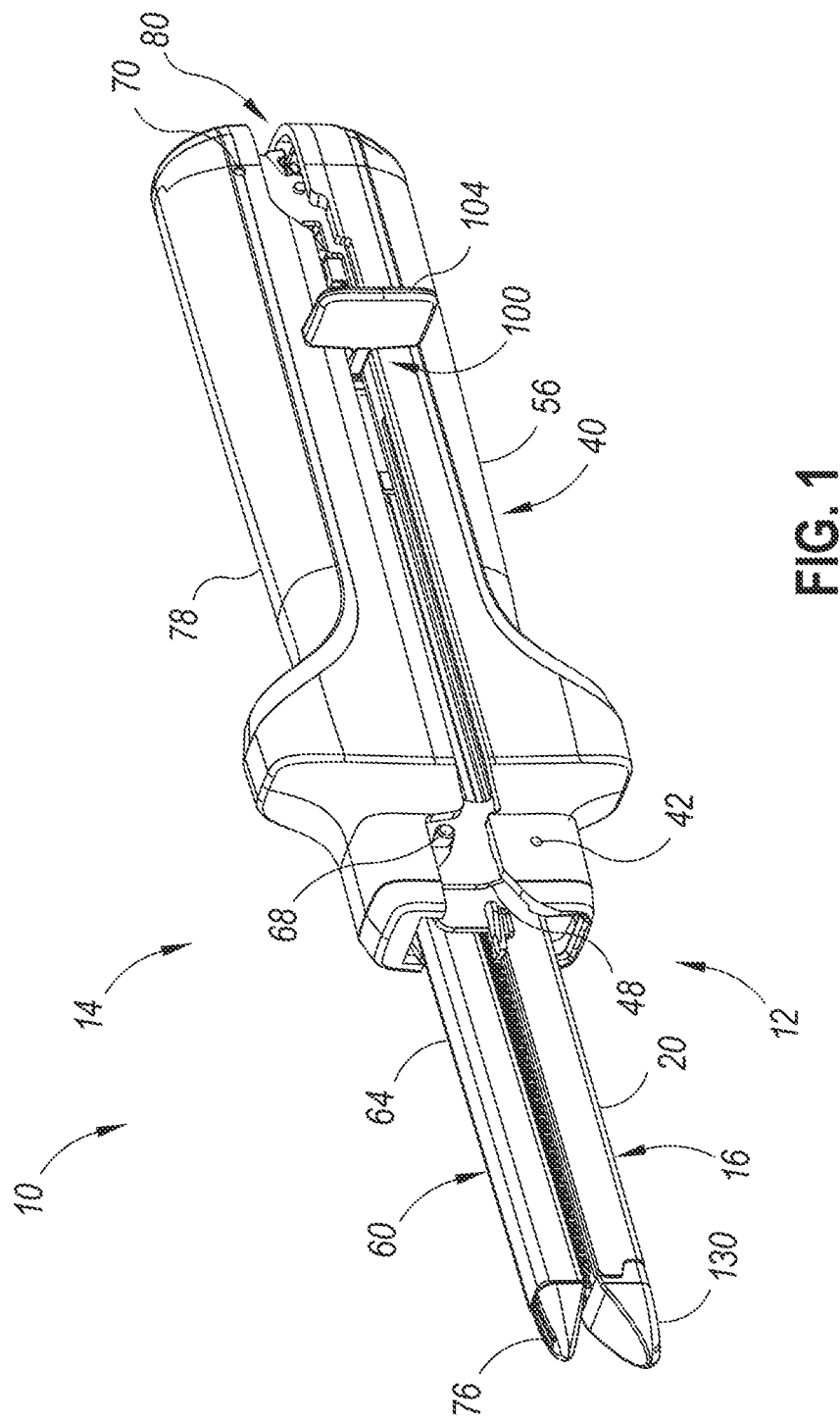
FIG. 1 depicts a perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. EXEMPLARY LINEAR SURGICAL STAPLER

A. Overview of Linear Surgical Stapler

Figure 2:
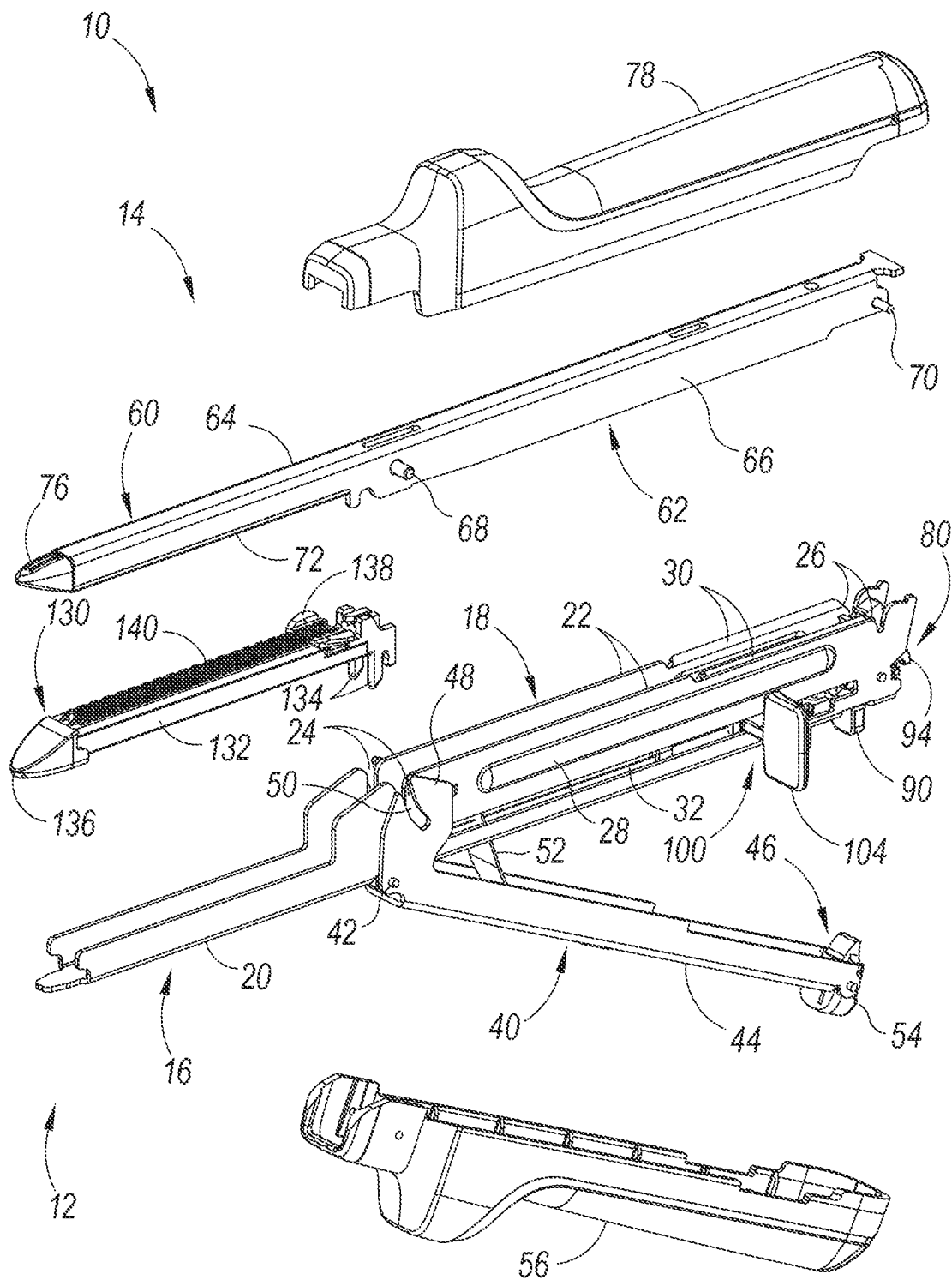
FIG. 2 depicts an exploded perspective view of the linear surgical stapler of FIG. 1.

FIGS. 1-2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) includes an elongate cartridge channel (16) having a proximal frame portion (18) and a distal jaw portion (20). Proximal frame portion (18) slidably retains a firing assembly (100) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (100) between proximal and distal positions. Firing assembly (100) is described in greater detail below in connection with FIG. 4. Distal jaw portion (20) of cartridge channel (16) is configured to receive a staple cartridge (130) (or "reload"), which may be configured in accordance with the teachings of U.S. patent application Ser. No. 16/537,005, entitled "Linear Surgical Stapler," filed on Aug. 9, 2019, issued as U.S. Pat. No. 11,229,433 on Jan. 25, 2022, the disclosure of which is incorporated by reference herein.

Cartridge half (12) further includes a clamp lever (40) (also referred to as a "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 3:
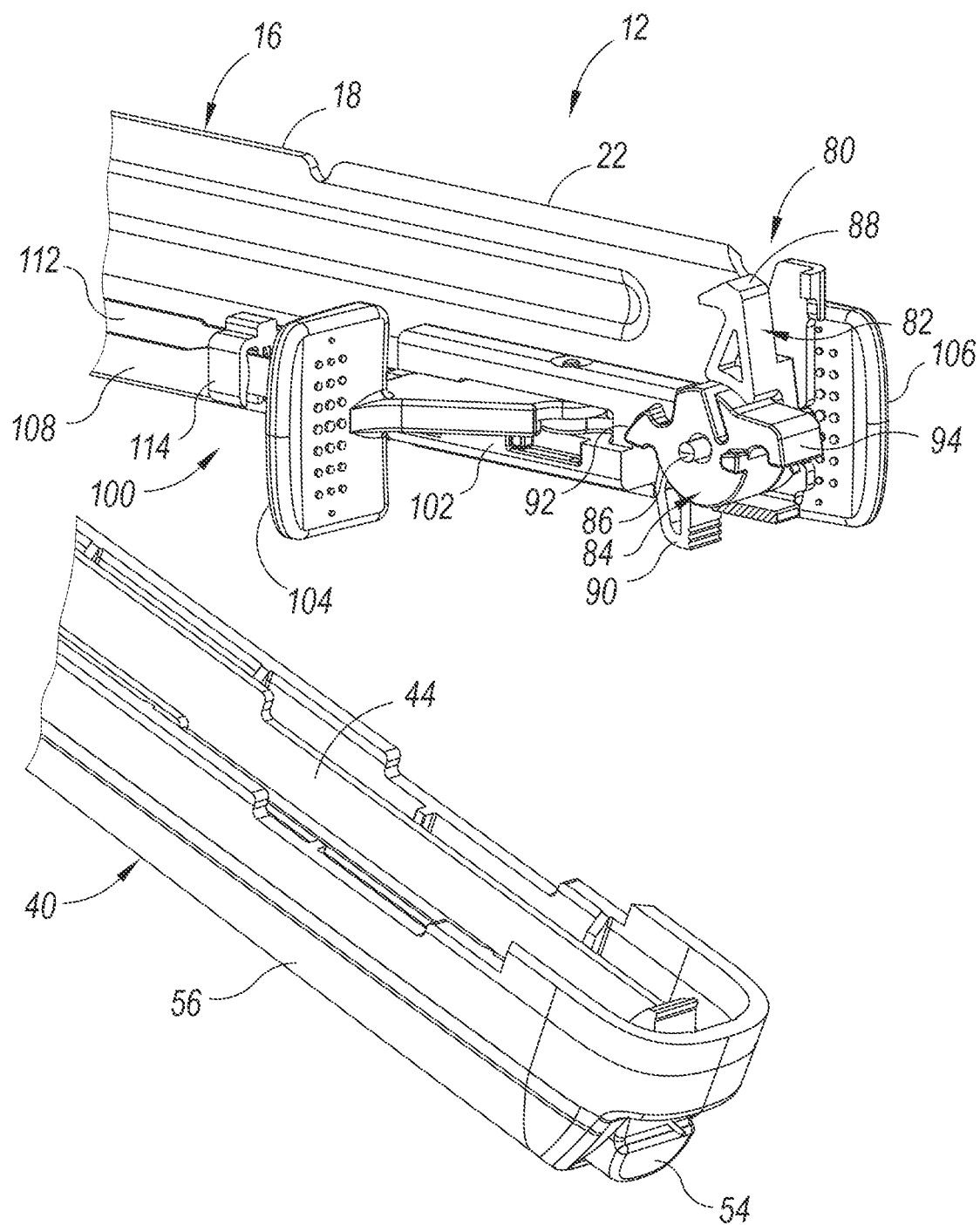
FIG. 3 depicts a perspective view of a proximal portion of the cartridge half of the linear surgical stapler of FIG. 1, showing a cartridge channel in cross-section and the clamp lever in an open position to reveal internal features of the cartridge half.

Clamp lever (40) is operable to pivot relative to cartridge channel (16) between an open position in which proximal end (46) of lever arm (44) is spaced from cartridge channel frame portion (18), and a closed position in which proximal end (46) confronts cartridge channel frame portion (18). Actuation of clamp lever (40) from the open position to the closed position operates to capture the opposed lateral ends of latch pin (68) within clamp lever jaw slots (50), and thereby clamp anvil half (14) against cartridge half (12), as shown and described below in connection with FIGS. 5C-5D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a flat spring (52) biases lever arm (44) toward the open position. Accordingly, flat spring (52) promotes disengagement of clamp lever jaws (48) from anvil half latch pin (68) upon initial advancement of clamp lever (40) from the closed position toward the open position. As best shown in FIGS. 2 and 3, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired.

Anvil half (14) of linear surgical stapler (10) includes an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil pins (68, 70) are configured to facilitate coupling of anvil half (14) with cartridge half (12), as described below.

Distal jaw portion (64) of anvil half (14) supports an anvil plate (72) that defines an anvil surface having a plurality of staple forming pockets (not shown) configured to deform legs of staples ejected by staple cartridge (130) when stapler (10) is fired, for example as described in greater detail in U.S. patent application Ser. No. 16/537,005, issued as U.S. Pat. No. 11,229,433 on Jan. 25, 2022, incorporated by reference above. In some versions, the anvil surface may be formed integrally with distal jaw portion (64). Distal jaw portion (64) of anvil half (14) additionally supports a tapered distal tip member (76). In some versions, distal tip member (76) may be selectively extendable relative to distal jaw portion (64) in accordance with the teachings of U.S. patent application Ser. No. 16/165,587, entitled "Decoupling Mechanism for Linear Surgical Stapler," filed on Oct. 19, 2018, issues as U.S. Pat. No. 11,033,266 on Jun. 15, 2021, the disclosure of which is incorporated by reference herein.

As shown in FIG. 2, linear surgical stapler (10) further includes a plurality of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) in accordance with the teachings of U.S. patent application Ser. No. 16/102,170, entitled "Clamping Assembly for Linear Surgical Stapler," filed on Aug. 13, 2018, published as U.S. Pub. No. 2020/0046353 on Feb. 13, 2020, issued as U.S. Pat. No. 11,278,285 on Mar. 22, 2022, the disclosure of which is incorporated by reference herein. It will be appreciated that in other versions, shrouds (56, 78) may be coupled with clamp lever (40) and anvil channel (60) in a variety of other suitable manners readily apparent to those of ordinary skill in the art.

As shown best in FIG. 3, a proximal end of cartridge half (12) includes a retaining assembly (80) configured to releasably retain portions of anvil half (14) and firing assembly (100). Retaining assembly (80) of the present example includes an anvil latch member (82) and a detent member (84), both of which are rotatably coupled with a proximal end of cartridge channel (16) via a laterally extending pin (86) arranged proximally of firing slots (32). A torsion spring (not shown) is configured to resiliently bias anvil latch member (82) and detent member in opposite rotational directions about the lateral axis defined by pin (86).

Anvil latch member (82) includes an upper finger (88) configured to releasably capture proximal anvil pin (70) when pin (70) is directed into proximal tapered notches (26) of cartridge channel (16), thereby coupling the proximal ends of stapler halves (12, 14). A lower end of anvil latch member (82) defines a release button (90) configured to be depressed by the operator when clamp lever (40) is in the open position to release proximal pin (70) from latch finger (88) and thereby permit separation of the proximal ends of stapler halves (12, 14). Detent member (84) includes a distal finger (88) configured to releasably capture the proximal end of a slide block (102) of firing assembly (100) when firing assembly (100) us in a proximal home position, shown in FIG. 3. Detent member (84) further includes a proximal hook (94) configured to releasably capture an upper tip of clamp lever latch member (54) while slide block (102) is positioned distally of its proximal home position, thereby preventing actuation of clamp lever latch member (54) and opening of clamp lever (40) during firing of stapler (10). When firing assembly (100) is in its proximal home position (i.e., before or after firing of stapler (10)), proximal hook (94) of detent member (84) permits clamp lever latch member (54) to rotatably disengage proximal frame portion (18) of cartridge channel (16) in response to actuation by the operator. As a result, clamp lever (40) may then be opened. Retaining assembly (80) and related components of cartridge half (12) may be further configured and operable in accordance with at least some of the teachings of U.S. patent application Ser. No. 16/102,164, entitled "Firing System for Linear Surgical Stapler," filed on Aug. 13, 2018, issued as U.S. Pat. No. 10,898,187 on Jan. 26, 2021, the disclosure of which is incorporated by reference herein.

Figure 4:
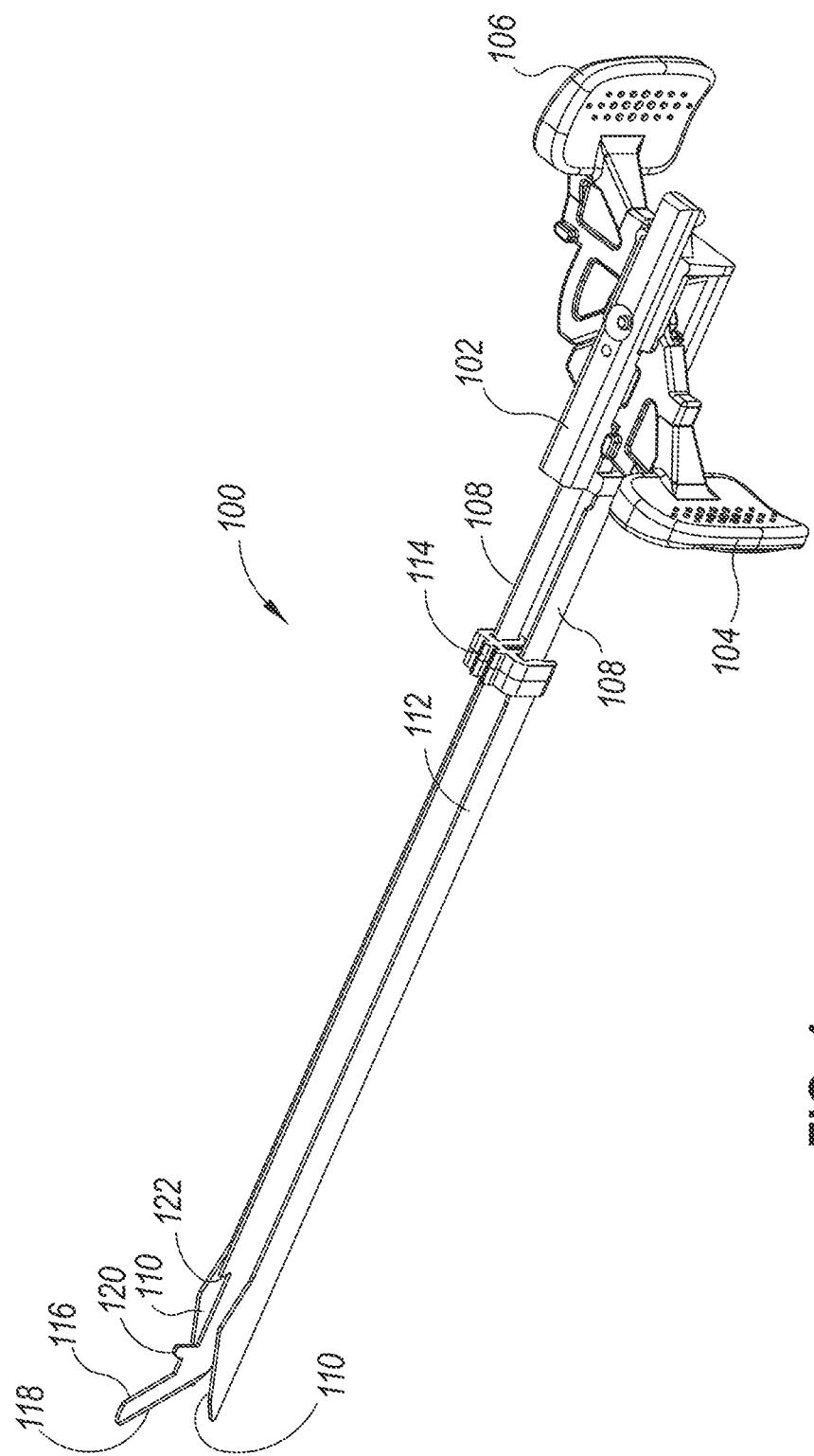
FIG. 4 depicts a top perspective view of a firing assembly of the linear surgical stapler of FIG. 1.

As shown best in FIG. 4, firing assembly (100) of cartridge half (12) includes slide block (102), a pair of actuators (104, 106) (or "firing knobs") pivotably coupled to slide block (102), and a plurality of elongate beams (108, 112) extending distally from slide block (102). A pair of side beams (108) are coupled at their proximal ends to a distal end of slide block (102) and terminate distally in a pair of cam ramps (110). Cam ramps (110) are configured to engage the undersides of staple drivers (not shown) housed within staple cartridge (130) and actuate staple drivers upwardly to thereby drive (or "fire") staples from cartridge (130) into tissue clamped between staple cartridge (130) and anvil plate (72). A center beam (112) is coupled with side beams (108) via a bridge member (114) (or "knife block") spaced distally from slide block (102). Center beam (112) terminates distally in a distally angled knife member (116) having a distal cutting edge (118) configured to cut tissue clamped between the distal portions of stapler halves (12, 14). A distal portion of center beam (112) additionally includes an upwardly projecting stop element (120) proximal to knife member (116), and a distally facing lockout projection (122) proximal to stop element (120).

Each actuator (104, 106) of firing assembly (100) is configured and rotatable relative to slide block (102) between a deployed position and a retracted position such that only one actuator (104, 106) may be deployed at a time, for example as described in greater detail in U.S. patent application Ser. No. 16/102,164, issued as U.S. Pat. No. 10,898,187 on Jan. 26, 2021, incorporated by reference above. In the deployed position, an actuator (104, 106) may be driven distally by an operator to actuate firing assembly (100) distally through stapler (10) and thereby simultaneously cut and staple tissue clamped between stapler halves (12, 14).

B. Overview of Exemplary Staple Cartridge

As best shown in FIG. 2, staple cartridge (130) includes an elongate cartridge body (132) extending linearly along a longitudinal axis between a proximal end having a pair of hooks (134) and a distal end having a tapered nose (136). Proximal hooks (134) are configured to releasably capture clamp lever pivot pin (42) and extend downwardly through corresponding openings formed in a floor of cartridge channel (16) when staple cartridge (130) is seated within distal jaw portion (20) of cartridge channel (16). A pair of wing tabs (138) disposed on the lateral sides of cartridge body (132) near the proximal end are configured to facilitate insertion and removal of staple cartridge (130) relative to distal jaw portion (20). An upper side of cartridge body (132) defines a deck (140). An elongate knife slot (not shown) extends longitudinally through deck (140) along the longitudinal axis of staple cartridge (130) and is configured to slidably receive knife member (116) of firing assembly (100) therethrough in response to distal actuation thereof, described above. A rigid tissue gap post (146) is secured at a distal end of the knife slot and protrudes upwardly away from cartridge deck (140). A rounded upper end of tissue gap post (146) is configured to contact a distal end of anvil plate (72) and thereby define a tissue gap between cartridge deck (140) and anvil plate (72) when stapler halves (12, 14) are clamped together in the manner described below. Staple cartridge (130) may be configured in accordance with U.S. patent application Ser. No. 16/537,005, issued as U.S. Pat. No. 11,299,433 on Jan. 25, 2022, incorporated by reference above.

C. Exemplary Use of Linear Surgical Stapler

Figure 5A:
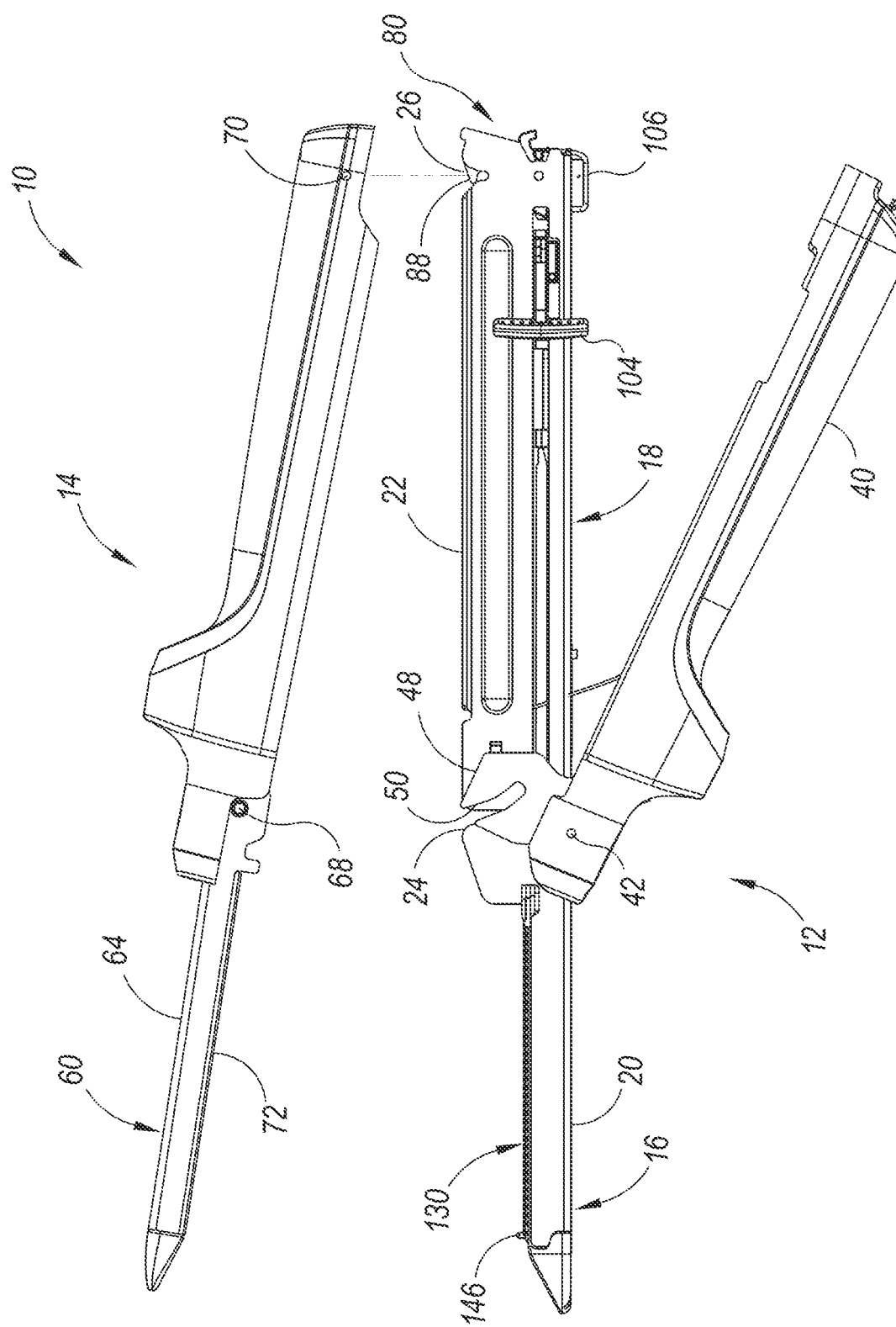
FIG. 5A depicts a side elevational view of the linear surgical stapler of FIG. 1, showing the stapler halves separated from one another.

FIGS. 5A-5E show exemplary coupling of stapler halves (12, 14) and subsequent firing of assembled stapler (10) during a surgical procedure. As shown in FIG. 5A, clamp lever (40) of cartridge half (12) is provided in the open position so that jaw slots (50) align with vertical slots (24) of cartridge channel side flanges (22). Additionally, firing assembly (100) is maintained in its proximal home position by detent member (84) of retaining assembly (80), as shown in FIG. 3 described above. At this stage, a section of tissue (not shown) to be stapled and cut may be positioned over the top of staple cartridge (130) disposed in distal jaw portion (20) of cartridge half (12). Alternatively, the tissue may be positioned over staple cartridge (130) following coupling of the proximal ends of stapler halves (12, 14), described below.

Figure 5B:
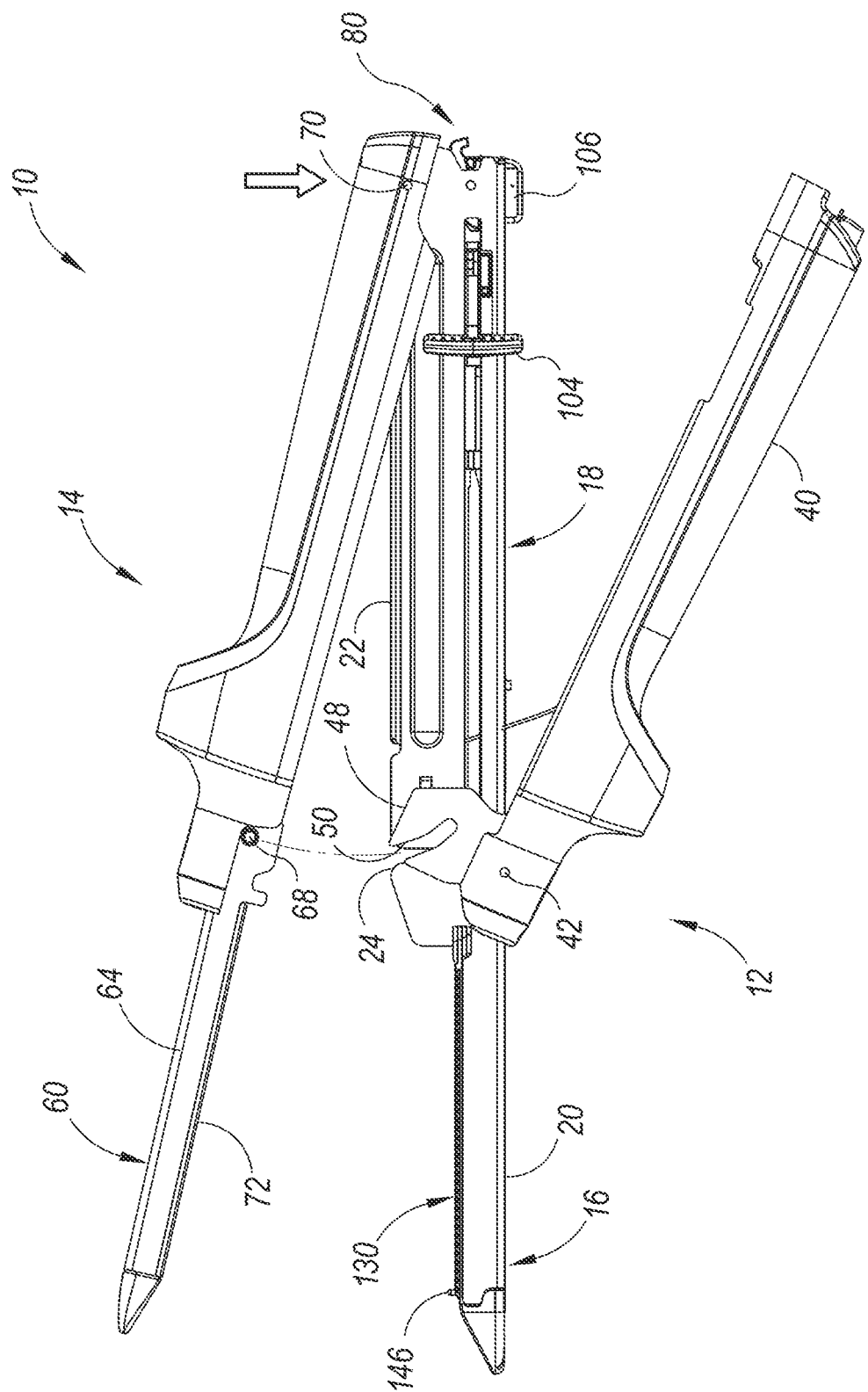
FIG. 5B depicts a side elevational view of the linear surgical stapler of FIG. 1, showing proximal ends of the stapler halves coupled together.
Figure 5C:
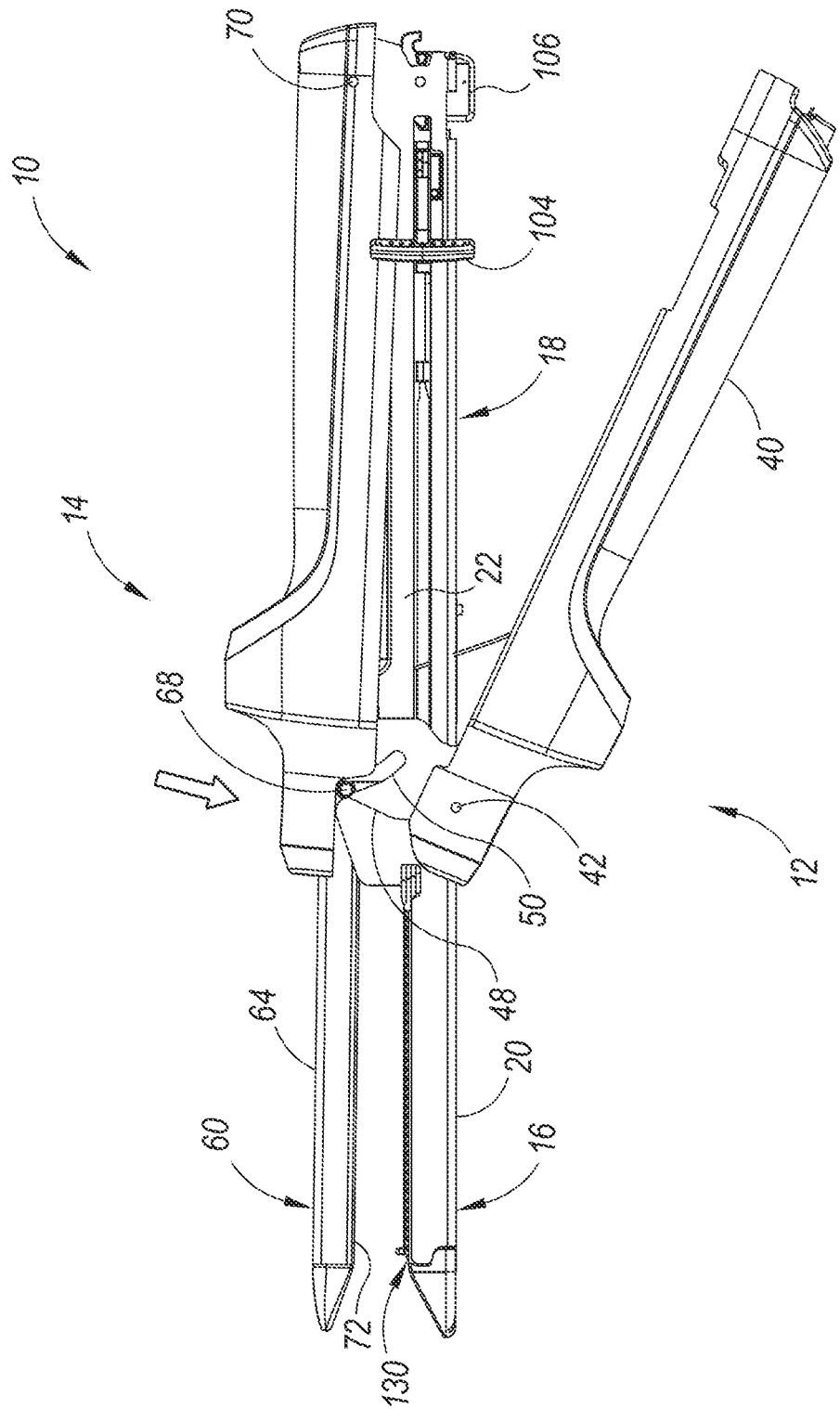
FIG. 5C depicts a side elevational view of the linear surgical stapler of FIG. 1, showing a distal pin of the anvil half being received by clamp lever jaws of the cartridge half.

As shown in FIG. 5A-5B, the proximal ends of stapler halves (12, 14) are aligned with one another and proximal anvil pin (70) is directed downwardly into proximal tapered notches (26) of cartridge channel (16) to engage upper finger (88) of anvil latch member (82). This engagement forces anvil latch member (82) to resiliently rotate clockwise, thus enabling upper finger (88) of anvil latch member (82) to capture anvil pin (70) and thereby releasably couple together the proximal ends of stapler halves (12, 14), as seen in FIG. 5B. As shown in FIG. 5C, and with clamp lever (40) remaining in the open position, anvil half (14) is rotated toward anvil half (14) about proximal anvil pin (70) so that distal latch pin (68) of anvil half (14) is received into vertical slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

Figure 5D:
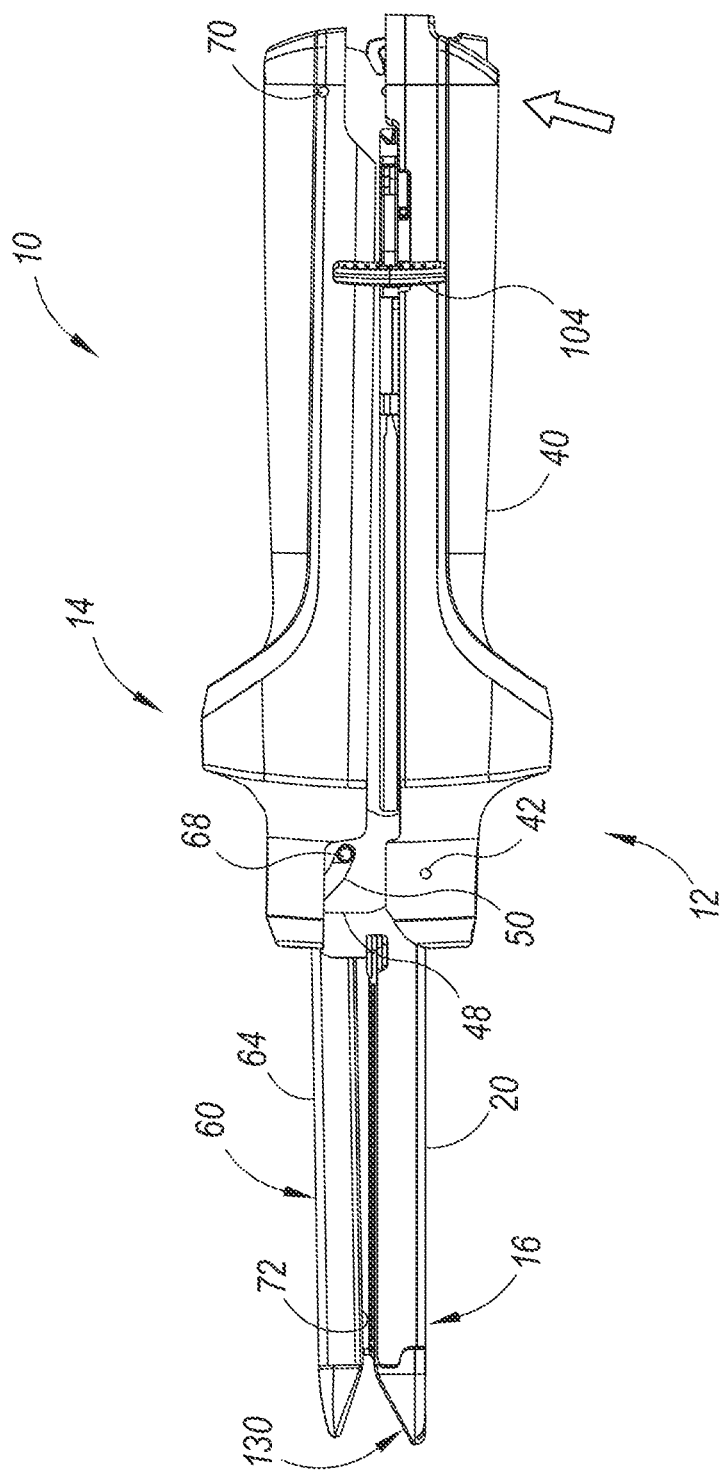
FIG. 5D depicts a side elevational view of the linear surgical stapler of FIG. 1, showing closure of the clamp lever to fully clamp the stapler halves together.

As shown in FIG. 5D, clamp lever (40) is closed to draw anvil latch pin (68) against the closed proximal ends of jaw slots (50) and thereby fully clamp anvil half (14) against cartridge half (12), with tissue (not shown) clamped between staple cartridge (130) and anvil plate (72). A slight transverse gap is defined between staple cartridge (130) and anvil plate (72) by tissue gap post (146) of staple cartridge (130), thus accommodating the tissue therebetween with a predetermined degree of tissue compression. As shown in FIGS. 5A and 5B, tissue gap post (146) is disposed at a distal end of staple cartridge (130) and is configured to contact a distal end of anvil plate (72) when stapler (10) is in the fully clamped state shown in FIG. 5D, for example as described in greater detail in U.S. patent application Ser. No. 16/537,005, issued as U.S. Pat. No. 11,229,433 on Jan. 25, 2022, incorporated by reference above.

Figure 5E:
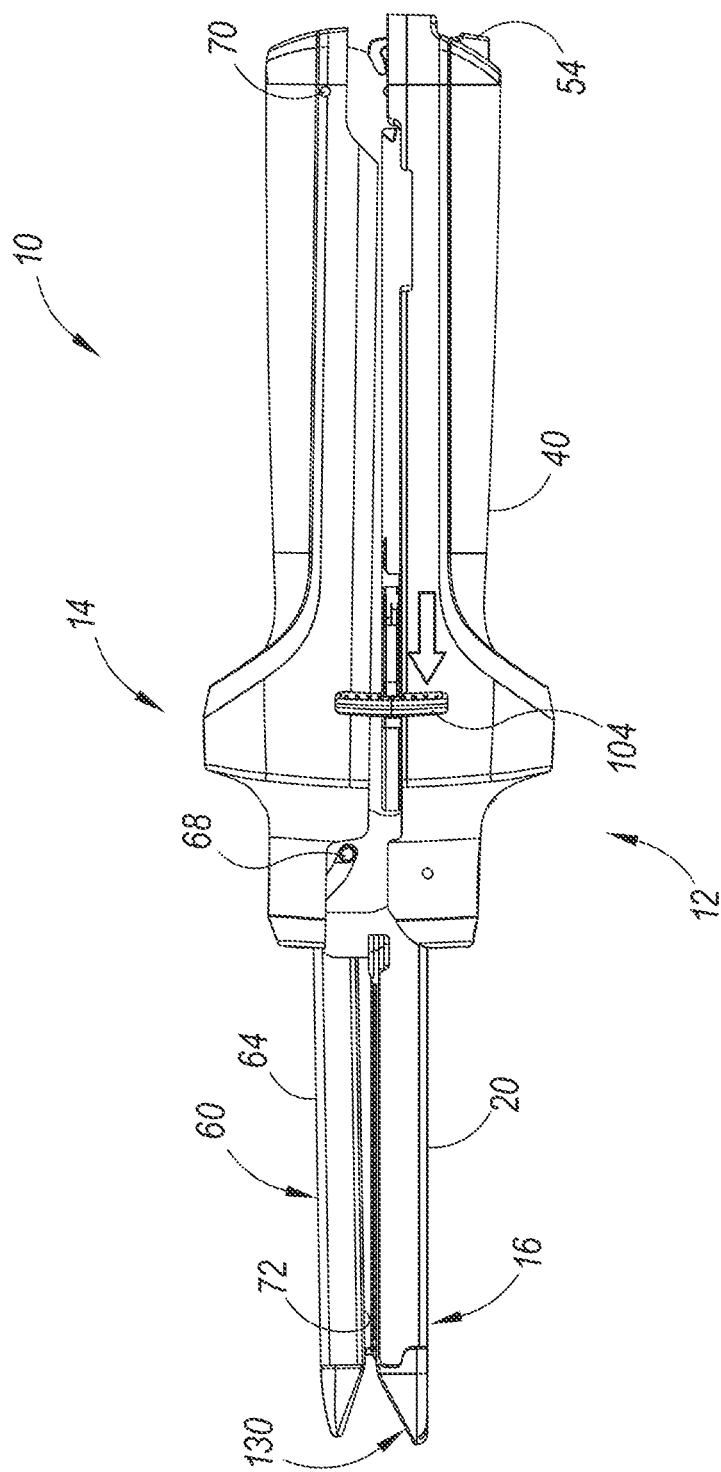
FIG. 5E depicts a side elevational view of the linear surgical stapler of FIG. 1, showing distal actuation of the firing assembly while the stapler halves are in the fully clamped state.

As shown in FIG. 5E, upon reaching the fully clamped state, stapler (10) may be fired by driving a deployed actuator (104, 106) of firing assembly (100) distally along proximal frame portion (18) of cartridge half (12). As described above in connection with FIG. 4, this action causes elongate beams (108, 112) of firing assembly (100) to translate distally through corresponding channels formed in staple cartridge (130) and thereby fire staples into the clamped tissue via cam ramps (110) and staple drivers, and simultaneously cut the clamped tissue with knife member (116). Following completion of the firing stroke, firing assembly (100) is returned to its proximal home position via the actuator (104, 106). Clamp lever latch member (54) may then be depressed to release the proximal end of clamp lever (40) from cartridge channel (16), thus permitting clamp lever (40) to be re-opened. Then, release button (90) of retaining assembly (80) may be depressed to release anvil half (14) from cartridge half (12) so that stapler halves (12, 14) may be separated from one another, thereby releasing the newly stapled and severed tissue. It will be understood that in some versions, stapler (10) may include features that promote decoupling of stapler halves (12, 14) similar to those features disclosed in U.S. patent application Ser. No. 16/165,587, issued as U.S. Pat. No. 11,033,266 on Jun. 15, 2021, incorporated by reference above.

II. EXEMPLARY SURGICAL LINEAR CUTTER PIN TRAP MECHANISMS

As described above in connection with surgical stapler (10), a pivotable coupling is established between the proximal ends of stapler halves (12, 14) when proximal anvil pin (70) is captured by upper finger (88) of anvil latch member (82). Release button (90) of retaining assembly (80) may be subsequently depressed to rotate upper finger (88) and thereby release anvil half (14) from cartridge half (12) so that stapler halves (12, 14) may be separated from one another.

In some instances, it may be desirable to provide a linear surgical stapler with an open state in which respective elongate members of the stapler halves assume a predetermined maximum angular orientation relative to one another and remain releasably coupled together at their proximal ends (also referred to as a "hang open" or "open aperture" state), such that the stapler in the open state can be easily manipulated by an operator with a single hand. It may also be desirable for the operator to be able to separate the halves by intuitively actuating a linearly translatable mechanism to release the proximal pin. Such a configuration may protect against unintentional decoupling of the stapler halves during single-handed manipulation of the stapler while also simplifying desired separations of the stapler halves. The following description provides several illustrative examples of variations of surgical stapler (10) that may provide such functionality.

A. Exemplary Linear Cutter Pin Trap Mechanism with Proximal Pin Capturing Slide

Figure 6:
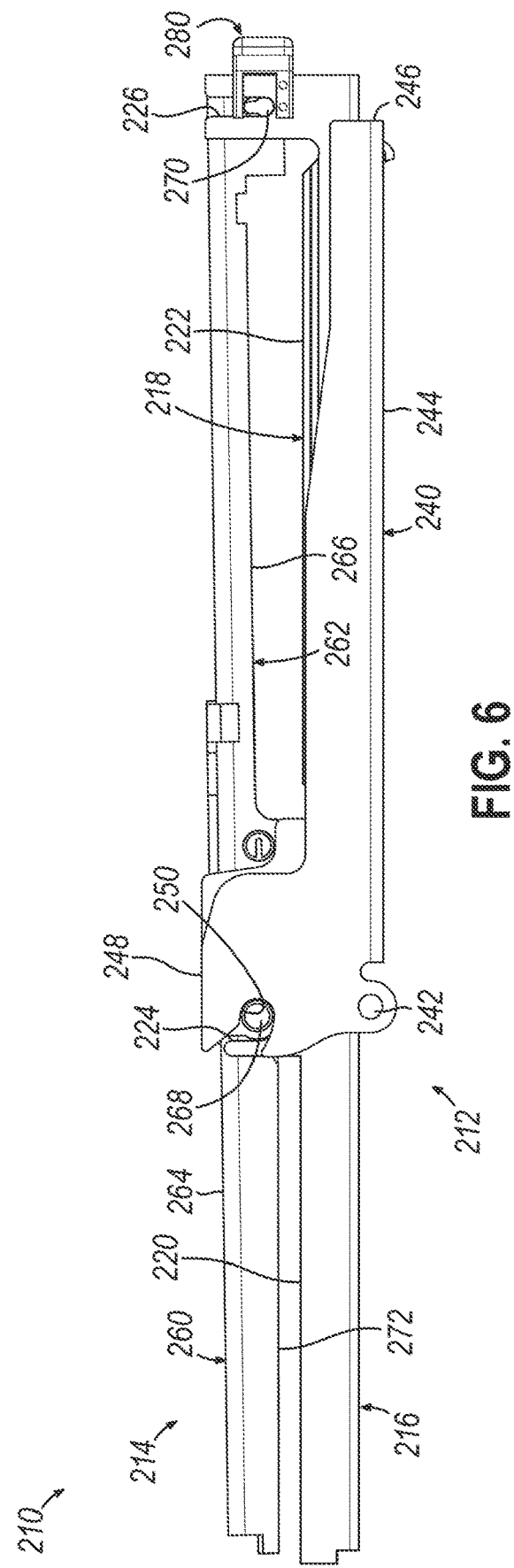
FIG. 6 depicts a side elevational view of another exemplary linear surgical stapler having a translatable locking member or slide positioned on the cartridge half, showing the stapler halves rotated toward each other in a clamped state.
Figure 7A:
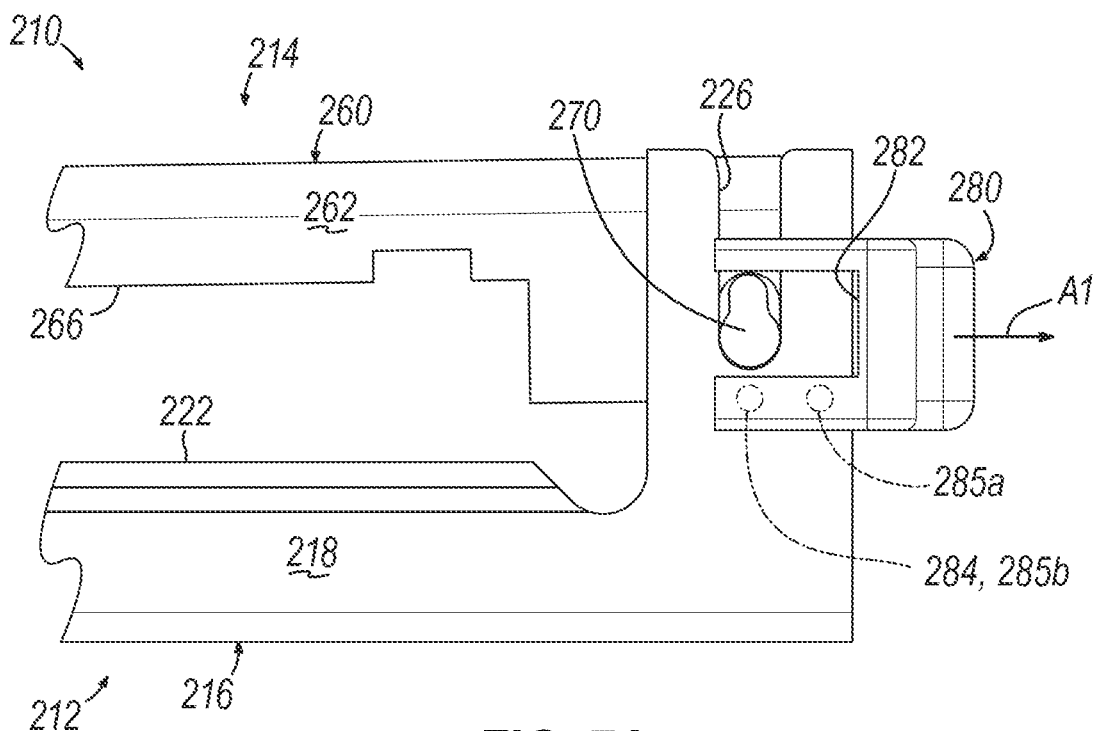
FIG. 7A depicts a side elevational view of a proximal end of the linear surgical stapler of FIG. 6, showing the slide of the cartridge half in a locked state capturing the proximal anvil pin for coupling the stapler halves at their proximal ends.
Figure 7B:
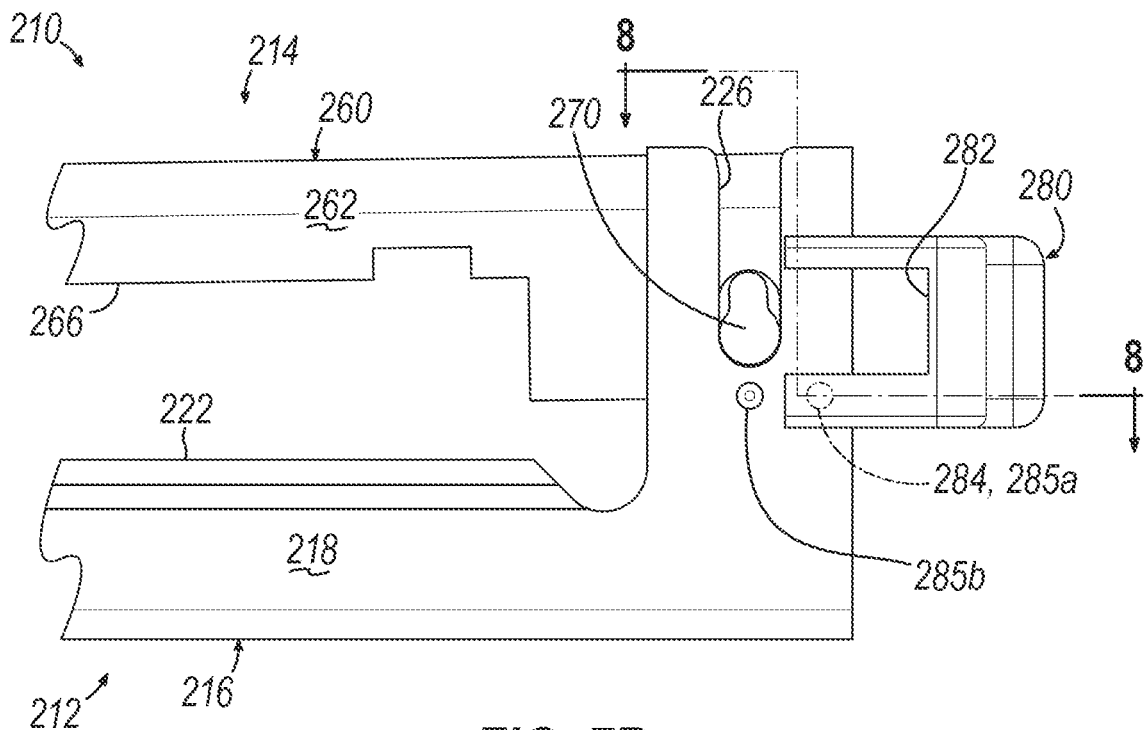
FIG. 7B depicts a side elevational view of the proximal end of the linear surgical stapler of FIG. 6, showing the slide of the cartridge half in an unlocked state releasing the proximal anvil pin for separating the stapler halves.
Figure 8:
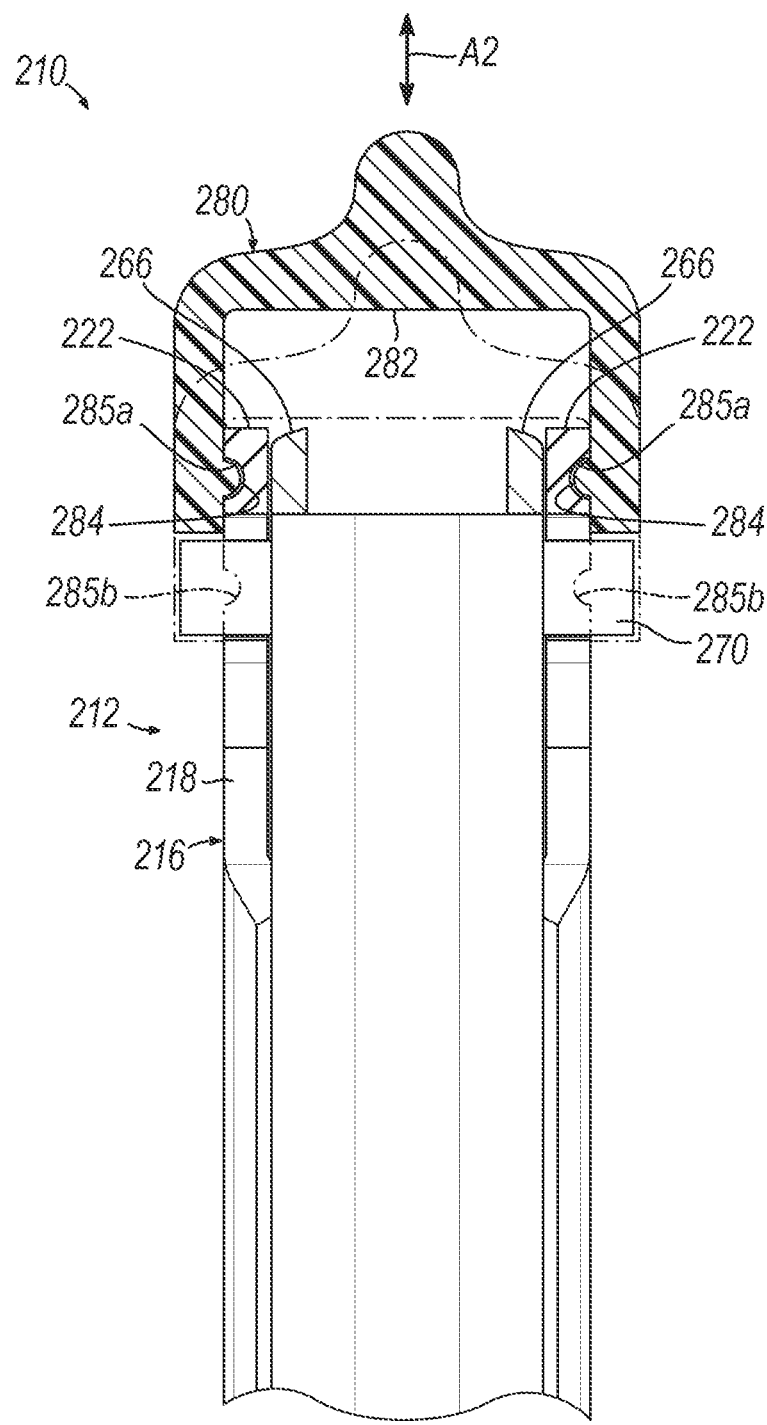
FIG. 8 depicts a cross sectional view of the proximal end of the linear surgical stapler of FIG. 6, taken along section line 8-8 in FIG. 7B, showing translation of the slide between the unlocked and locked states.

FIGS. 6-8 show an exemplary surgical stapler (210) including a cartridge half (212) and an anvil half (214) configured to remain releasably coupled together at their proximal ends in an open state in which respective elongate members of the stapler halves (212, 214) assume a predetermined maximum angular orientation relative to one another, and further configured to be pulled or pried apart from each other to allow separation of stapler halves (212, 214) from each other. Stapler (210) is similar to stapler (10) described above except as otherwise described below.

Cartridge half (212) of linear surgical stapler (210) includes an elongate cartridge channel (216) having a proximal frame portion (218) and a distal jaw portion (220). Proximal frame portion (218) slidably retains a firing assembly (not shown) and includes a laterally opposed pair of upright side flanges (222). Each side flange (222) includes a vertical slot (224) arranged at a distal end thereof, and a notch (226) arranged at a proximal end thereof. In the example shown, each side flange (222) extends upwardly to varying degrees along the length of proximal frame portion (218), such that the proximal portion of each side flange (222) defining the respective notch (226) is generally goal-post-shaped. It will be appreciated that side flanges (222) may be configured in any other suitable manner For example, one or both side flanges (222) may extend upwardly in a more uniform manner along the length of proximal frame portion (218) as shown in connection with stapler (10).

Cartridge half (212) further includes a clamp lever (240) pivotably coupled to cartridge channel (216) with a clamp lever pivot pin (242), which is arranged in approximate alignment with distal slots (224) of cartridge channel side flanges (222). Clamp lever (240) includes an elongate lever arm (244) having a free proximal end (246) and a distal end that is pivotably coupled to a lower portion of cartridge channel (216) with pivot pin (242). A pair of opposed jaws (248) extend distally from the distal end of lever arm (244) alongside cartridge channel side flanges (222). Each jaw (248) includes a curved slot (250) having a closed proximal end and an open distal end configured to receive a latch pin (268) of anvil half (214), as described above in connection to FIGS. 5A-5E.

Anvil half (214) of linear surgical stapler (210) includes an elongate anvil channel (260) having a proximal frame portion (262) and a distal jaw portion (264). Proximal frame portion (262) includes a laterally opposed pair of upright side flanges (266) that are configured to be received between cartridge channel side flanges (222) when anvil half (214) is coupled with cartridge half (212). A distal latch projection in the form of latch pin (268) extends laterally through the distal ends of anvil channel side flanges (266), and a proximal pivot projection in the form of a generally pear-shaped proximal pin (270) extends laterally through the proximal ends of anvil channel side flanges (266). Distal jaw portion (264) of anvil half (214) supports an anvil plate (272) that defines an anvil surface having a plurality of staple forming pockets (not shown) configured to deform legs of staples ejected by a staple cartridge (not shown) when stapler (210) is fired.

As shown best in FIGS. 7A-8, cartridge half (212) further includes a longitudinally translatable locking member or slide (280) defining a distally open-ended aperture (282) configured to releasably retain proximal anvil pin (270). The illustrated slide (280) further includes a laterally opposed pair of detent members (284) positioned below a lower peripheral edge of aperture (282) and extending laterally inwardly for facilitating releasable coupling of slide (280) to cartridge channel (216).

In this regard, cartridge half (212) further includes laterally opposed pairs of proximal and distal indent members (285a, 285b) positioned on respective side flanges (222) and configured to selectively receive respective detent members (284) with a friction fit or a snap fit for coupling slide (280) to cartridge channel (216). In this manner, selective engagement between detent members (284) and distal indent members (285b) may secure slide (280) to the goalpost-shaped proximal portions of side flanges (222) with aperture (282)

longitudinally aligned with notches (226) to define a "locked" state of slide (280), as shown in FIG. 7A Likewise, selective engagement between detent members (284) and proximal indent members (285a) may secure slide (280) to the goalpost-shaped proximal portions of side flanges (222) with aperture (282) positioned proximally relative to notches (226) to define an "unlocked" state of slide (280), as shown in FIG. 7B.

As best shown in FIG. 7A, aperture (282) of slide (280) is configured to cooperate with notches (226) to releasably and pivotably capture proximal anvil pin (270) when proximal anvil pin (270) is received within proximal notches (226) with slide (280) in the locked state, thereby coupling the proximal ends of stapler halves (212, 214). More particularly, aperture (282) is sized and configured to permit rotation of proximal anvil pin (270) therewithin to accommodate rotation of anvil half (214) about proximal anvil pin (270).

In this regard, an upper peripheral edge of aperture (282) may be configured to rotatably sandwich proximal anvil pin (270) against closed ends of notches (226) to prevent proximal anvil pin (270) from being inadvertently dislodged from notches (226) while slide (280) is in the locked state. For example, the upper peripheral edge of aperture (282) may be configured to continuously confront proximal anvil pin (270) during rotation of anvil half (214) away from cartridge half (212) to a predetermined maximum orientation whereat a narrow upper portion of proximal anvil pin (270) abuts proximal surfaces of notches (226) to assist in preventing inadvertent decoupling of stapler halves (212, 214), such as during single-handed manipulation of stapler (210). In this manner, such interaction between aperture (282) and proximal anvil pin (270) may assist in defining an open state of stapler (210) by allowing cartridge half (212) and anvil half (214) to remain releasably coupled together at their proximal ends while their distal ends are spaced apart by an open gap. Thus, interaction between aperture (282) and proximal anvil pin (270) may assist in reliably coupling anvil half (214) to cartridge half (212) during rotation of anvil half (214) about proximal anvil pin (270) between the open and clamped states.

As best shown in FIG. 8, detent members (284) are sized relative to proximal and distal indent members (285a, 285b) (e.g., in the lateral direction) to permit selective overriding of the interaction therebetween upon application of a threshold longitudinal force applied between slide (280) and cartridge channel (216) to thereby withdraw detent members (284) from indent members (285a, 285b) for moving slide (280) between the locked and unlocked states, and/or for separating slide (280) from cartridge channel (216), as indicated by first and second arrows (A1, A2) in FIGS. 7A and 8, respectively.

Figure 9A:
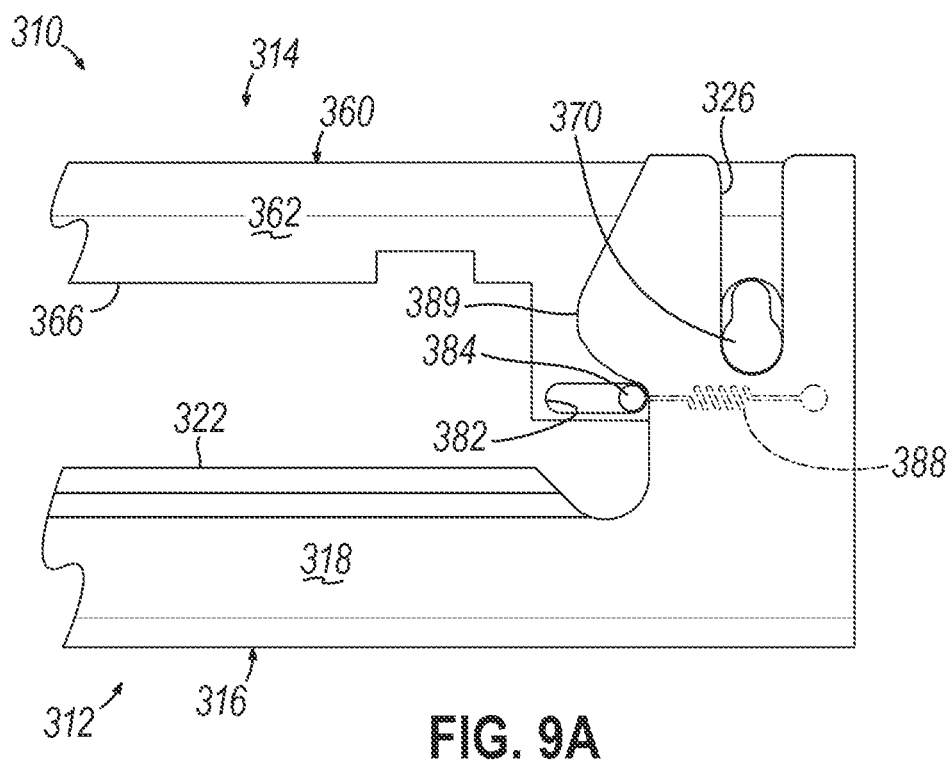
FIG. 9A depicts a side elevational view of a proximal end of another exemplary linear surgical stapler having an anvil half with a proximally-biased pin and a cartridge half with a corresponding camming surface for coupling the stapler halves at their proximal ends, showing the stapler halves biased toward the clamped state.
Figure 9B:
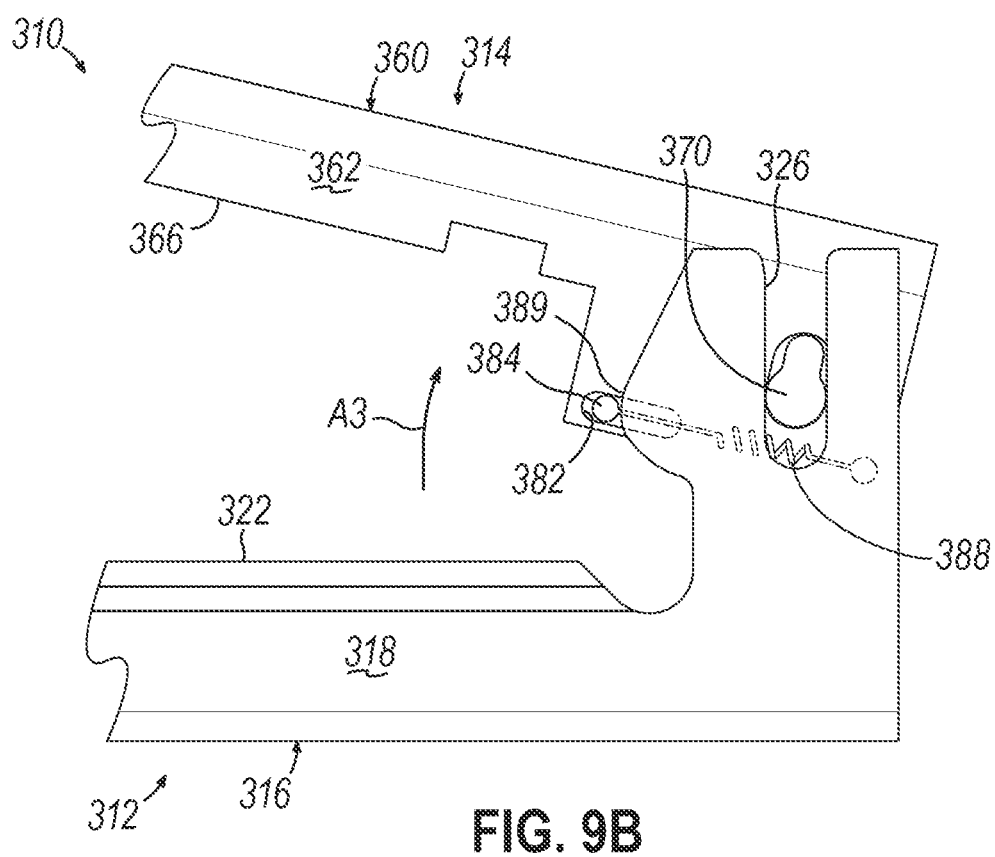
FIG. 9B depicts a side elevational view of the proximal end of the linear surgical stapler of FIG. 9A, showing rotation of the anvil half away from the cartridge half to direct the pin over a distal apex of the camming surface for separating the stapler halves.
Figure 9C:
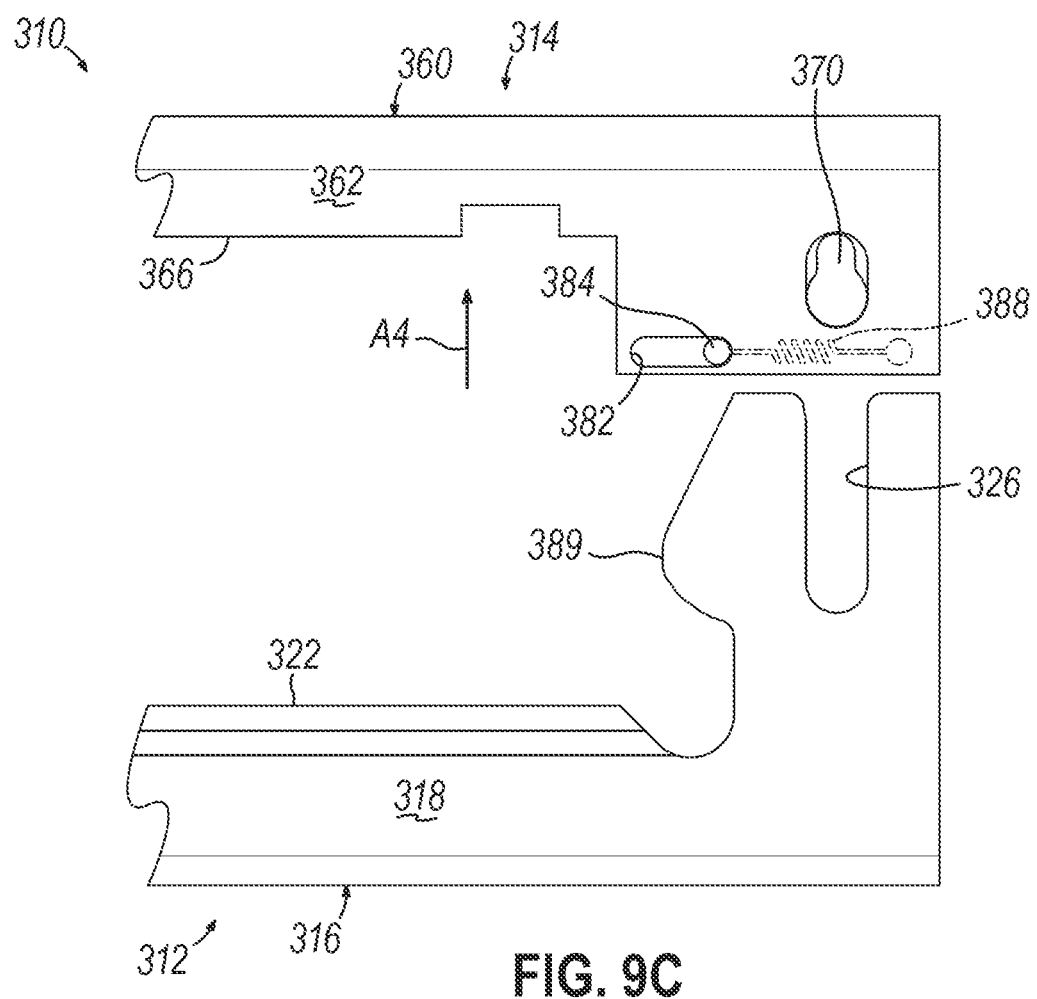
FIG. 9C depicts a side elevational view of the proximal end of the linear surgical stapler of FIG. 9A, showing separation of the stapler halves.

B. Exemplary Linear Cutter Pin Trap Mechanism with Proximally-Biased Retention Pin on Anvil Half and Camming Surface on Cartridge Half In some instances, it may be desirable to provide a surgical stapler having a pin trap mechanism with resilient and camming features that cooperate to bias the stapler halves toward a clamped state. FIGS. 9A-9C show another exemplary surgical stapler (310) including a cartridge half (312) and an anvil half (314) that are configured in such a manner, and which are similar in structure and function to stapler (210) described above except as otherwise described below.

Cartridge half (312) includes an elongate cartridge channel (316) having a proximal frame portion (318) including a laterally opposed pair of upright side flanges (322), each including a notch (326) arranged at a proximal end thereof. Anvil half (314) includes an elongate anvil channel (360) having a proximal frame portion (362) including a laterally opposed pair of upright side flanges (366) that are configured to be received between cartridge channel side flanges (322) when anvil half (314) is coupled with cartridge half (312). A proximal pivot projection in the form of a generally pear-shaped proximal pin (370) extends laterally through the proximal ends of anvil channel side flanges (366).

In the example shown, a proximal end of anvil half (314) includes a laterally opposed pair of slots (382) extending longitudinally along respective side flanges (366) between closed ends slightly below and distal relative to proximal anvil pin (370). Anvil half (314) further includes a longitudinally translatable pin (384) positioned within and extending laterally outwardly from slots (382) such that lateral ends of pin (384) are capable of engaging cartridge side flanges (322). As shown, anvil half (314) also includes a resilient member in the form of a tension or extension spring (388) longitudinally aligned with slots (382) and having a proximal end fixed relative to anvil side flanges (366) and a distal end fixed relative to pin (384), such that spring (388) is configured to bias pin (384) toward the proximal closed ends of slots (382).

In this regard, a proximal end of cartridge half (312) includes a laterally opposed pair of camming surfaces (389) extending distally from the goalpost-shaped proximal portions of respective cartridge side flanges (322) and configured to selectively engage pin (384) for coupling stapler halves (312, 314). In the example shown, camming surfaces (389) are each generally rounded toward a distal apex and include a relatively steep lower portion and a relatively gradual upper portion.

As best shown in FIG. 9A, camming surfaces (389) of cartridge half (312) are configured to cooperate with proximally-biased pin (384) to assist in maintaining proximal anvil pin (370) within proximal notches (326), thereby coupling the proximal ends of stapler halves (312, 314). More particularly, spring (388) is configured to promote seating of pin (370) at lower bases of camming surfaces (389) and to resist distal movement of pin (370) along the steep lower portions of camming surfaces (389) toward the distal apexes thereof, thereby biasing stapler halves (312, 314) toward the clamped state. As best shown in FIG. 9B, camming surfaces (389) of cartridge half (312) are further configured to cooperate with proximally-biased pin (384) to permit decoupling of stapler halves (312, 314) upon application of a threshold rotational force applied between stapler halves (312, 314) sufficient to overcome the proximal biasing of pin (384) and thereby direct pin (384) toward the distal closed ends of slots (382) and over the distal apexes of camming surfaces (389) to the gradual upper portions thereof, as indicated by third arrow (A3) in FIG. 9B. With pin (384) positioned at or over the distal apexes of camming surfaces (389), anvil half (314) may be freely separable from cartridge half (312), as indicated by fourth arrow (A4) in FIG. 9C.

Figure 10A:
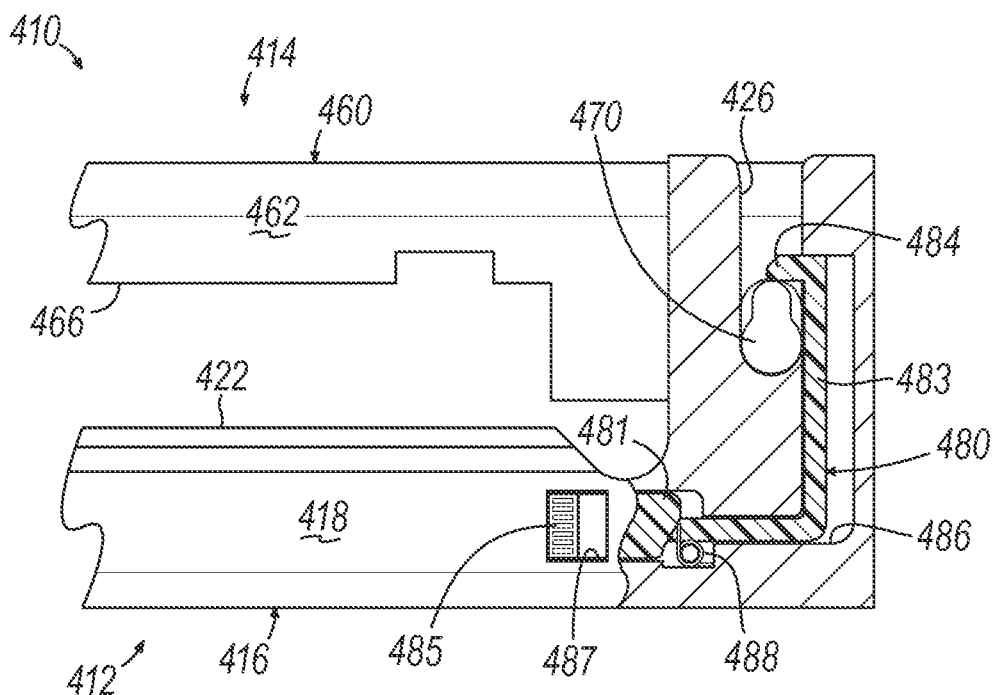
FIG. 10A depicts a partial cross sectional view of a proximal end of another exemplary linear surgical stapler having a distally-biased translatable locking member or slide positioned on the cartridge half, showing the slide of the cartridge half in a locked state capturing the proximal anvil pin for coupling the stapler halves at their proximal ends, and further showing the stapler halves rotated toward each other in a clamped state.
Figure 10B:
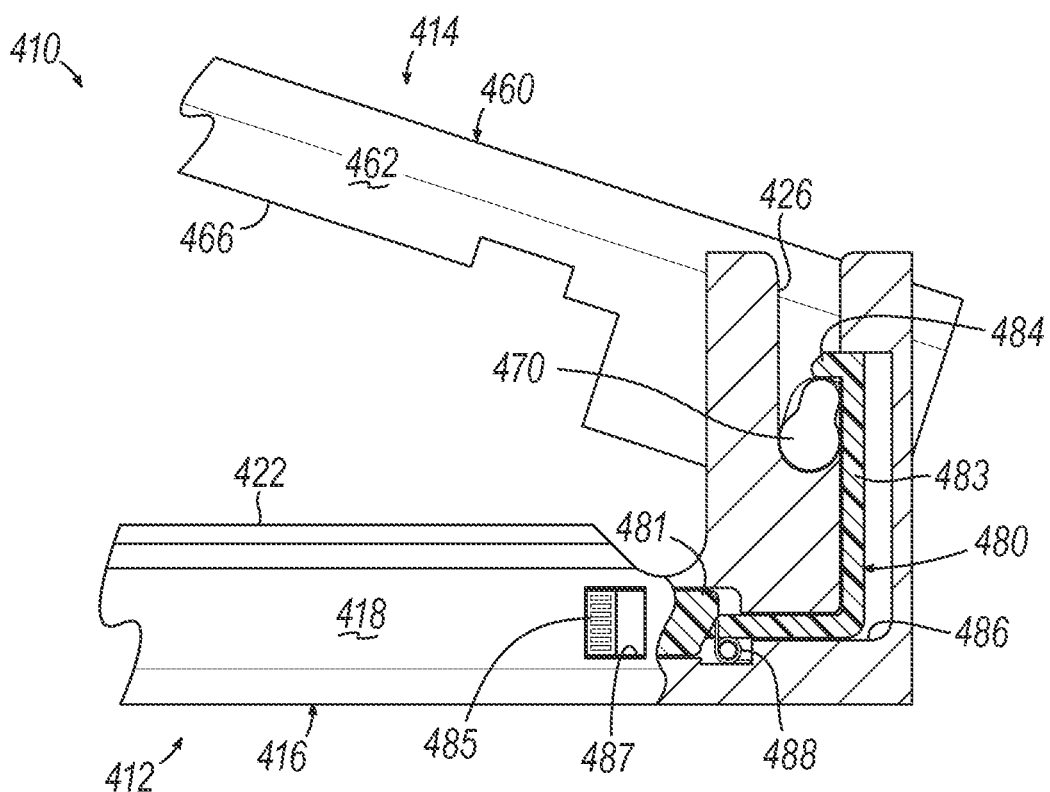
FIG. 10B depicts a partial cross sectional view of the proximal end of the linear surgical stapler of FIG. 10A, showing the slide of the cartridge half in a locked state capturing the proximal anvil pin for coupling the stapler halves at their proximal ends, and further showing the stapler halves rotated away from each other in an open state in which the proximal ends of the stapler halves are coupled together and the distal ends of the stapler halves are spaced apart.
Figure 10C:
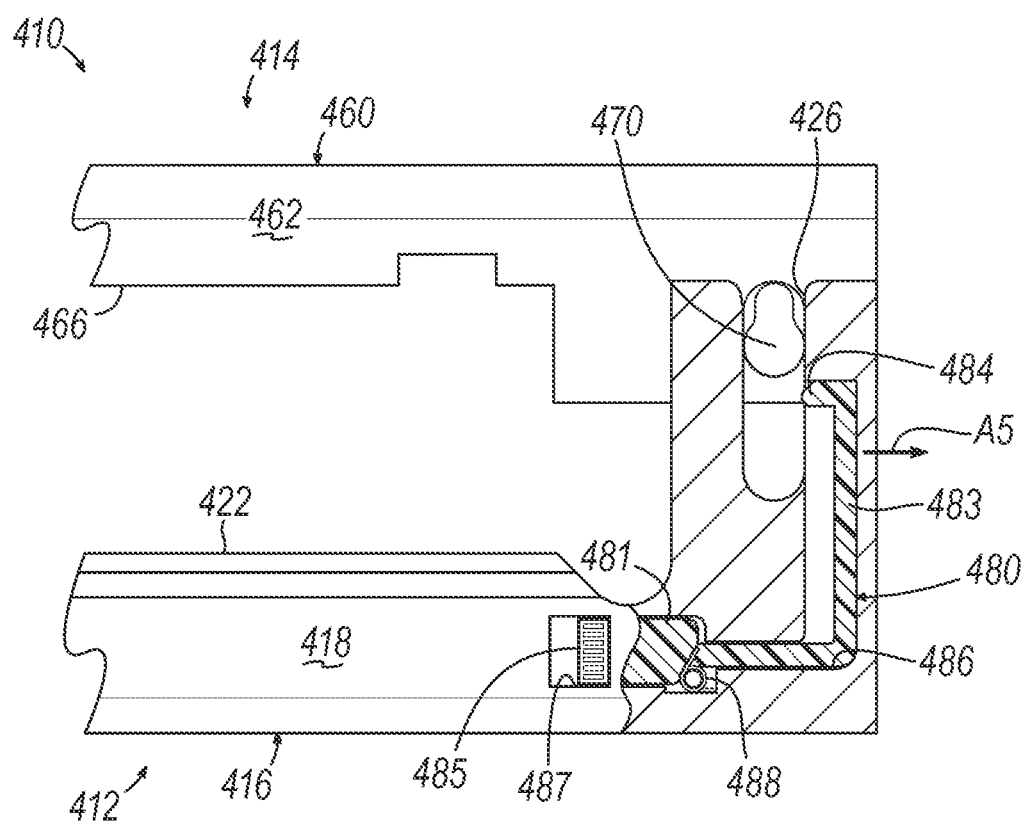
FIG. 10C depicts a partial cross sectional view of the proximal end of the linear surgical stapler of FIG. 10A, showing the slide of the cartridge half in an unlocked state releasing the proximal anvil pin for separating the stapler halves.

C. Exemplary Linear Cutter Pin Trap Mechanism with Distally-Biased Locking Member for Capturing Proximal Pin In some instances, it may be desirable to provide a surgical stapler having a pin trap mechanism that is distally biased. FIGS. 10A-10C show another exemplary surgical stapler (410) including a cartridge half (412) and an anvil half (414) that are configured in such a manner, and which are similar in structure and function to stapler (210) described above except as otherwise described below.

Cartridge half (412) includes an elongate cartridge channel (416) having a proximal frame portion (418) and a distal jaw portion (not shown). Proximal frame portion (418) includes a laterally opposed pair of upright side flanges (422), each including a notch (426) arranged at a proximal end thereof. Anvil half (414) includes an elongate anvil channel (460) having a proximal frame portion (462) and a distal jaw portion (not shown). Proximal frame portion (462) includes a laterally opposed pair of upright side flanges (466) that are configured to be received between cartridge channel side flanges (422) when anvil half (414) is coupled with cartridge half (412). A distal latch projection in the form of latch pin (not shown) extends laterally through the distal ends of anvil channel side flanges (466), and a proximal pivot projection in the form of a generally pear-shaped proximal pin (470) extends laterally through the proximal ends of anvil channel side flanges (466).

In the example shown, cartridge half (412) further includes a longitudinally translatable locking member or slide (480) having a longitudinal base (481), an arm (483) extending upwardly from a proximal end of base (481), and an upper finger or hook portion (484) extending distally from an upper end of arm (483) and configured to releasably retain proximal anvil pin (470). In the example shown, slide (480) further includes a button (485) extending laterally outwardly from base (481) and configured to assist an operator with gripping and manipulating slide (480). Cartridge half (412) also includes a cavity (486) configured to receive slide (480) and accommodate longitudinal translation of slide (480) therein between a distal locked state, as shown in FIGS. 10A and 10B, and a proximal unlocked state, as shown in FIG. 10C. As shown, cartridge half (412) further includes an aperture (487) configured to permit button (485) to extend laterally outwardly therethrough and accommodate longitudinal translation thereof corresponding to translation of slide (480) between the locked and unlocked states. In the example shown, button (485) and aperture (487) are both positioned at a side of cartridge half (412) with button surface (485) facing laterally outwardly, such that button surface (485) may be accessible via aperture (487) irrespective of whether a clamp lever (not shown) of stapler (410) is in an open or closed position. For example, button (485) and aperture (487) may remain unobstructed by the clamp lever when the clamp lever is in a closed position in which a proximal end of the clamp lever confronts cartridge channel frame portion (418). As shown, cartridge half (412) also includes a resilient member in the form of a torsion spring (488) positioned between base (481) and an interior surface of cavity (486), such that spring (488) is configured to bias slide (480) distally toward the locked state.

As best shown in FIGS. 10A and 10B, hook portion (484) of slide (480) is configured to cooperate with notches (426) to releasably and pivotably capture proximal anvil pin (470) when proximal anvil pin (470) is received within proximal notches (426) with slide (480) in the locked state, thereby coupling the proximal ends of stapler halves (412, 414). More particularly, hook portion (484) is sized and configured to permit rotation of proximal anvil pin (470) thereunder to accommodate rotation of anvil half (414) about proximal anvil pin (470).

In this regard, hook portion (484) of slide (480) may be configured to rotatably sandwich proximal anvil pin (470) against closed ends of notches (426) to prevent proximal anvil pin (470) from being inadvertently dislodged from notches (426) while slide (480) is in the locked state. For example, hook portion (484) of slide (480) may be configured to continuously confront proximal anvil pin (470) during rotation of anvil half (414) away from cartridge half (412) to a predetermined maximum orientation whereat a narrow upper portion of proximal anvil pin (470) abuts proximal surfaces of notches (426) and/or a distal surface of arm (483) to assist in preventing inadvertent decoupling of stapler halves (412, 414), such as during single-handed manipulation of stapler (410). In this manner, such interaction between hook portion (484) and proximal anvil pin (470) may assist in defining an open state of stapler (410) by allowing cartridge half (412) and anvil half (414) to remain releasably coupled together at their proximal ends while their distal ends are spaced apart by an open gap, as shown in FIG. 10B. Thus, interaction between hook portion (484) and proximal anvil pin (470) may assist in reliably coupling anvil half (414) to cartridge half (412) during rotation of anvil half (414) about proximal anvil pin (470) between the open and clamped states.

As best shown in FIG. 10C, button (485) may be configured to permit an operator to apply a threshold proximal force to slide (480) sufficient to overcome the distal biasing of slide (480) and thereby translate slide (480) to the unlocked state such that hook portion (484) is proximally withdrawn from proximal anvil pin (470) for separating stapler halves (412, 414), as indicated by fifth arrow (A5).

Though not shown, an opposite configuration of proximal pin (470) and slide (480) may be provided in which proximal pin (470) is provided on cartridge half (412) and slide (480) is provided on anvil half (414). In addition or alternatively, a double slide configuration may be provided in which proximal pin (470) (or any other suitable proximal pivot projection) is positioned on a longitudinally translatable slide and biased proximally toward pivotable engagement with hook portion (484) of slide (480). In such cases, the proximal pin slide may include a button portion configured to assist an operator with gripping and manipulating the proximal pin slide.

During operation, the operator may initially couple stapler halves (412, 414) together at their proximal ends by positioning proximal anvil pin (470) within notches (426) while applying a threshold proximal force to slide (480) to maintain slide (480) in the unlocked state, and by subsequently releasing slide (480) to allow spring (488) to urge slide (480) to the locked state to thereby capture proximal anvil pin (470) between hook portion (484) and the closed ends of notches (426). The operator may then rotate anvil half (414) relative to cartridge half (412) about proximal anvil pin (470) as desired, such as between the open and clamped states, while stapler halves (412, 414) remain reliably coupled to each other to perform a cutting and/or stapling procedure. If desired, the operator may selectively separate stapler halves (412, 414) from each other by translating slide (480) to the unlocked state to thereby release proximal anvil pin (470) from hook portion (484).

Figure 11:
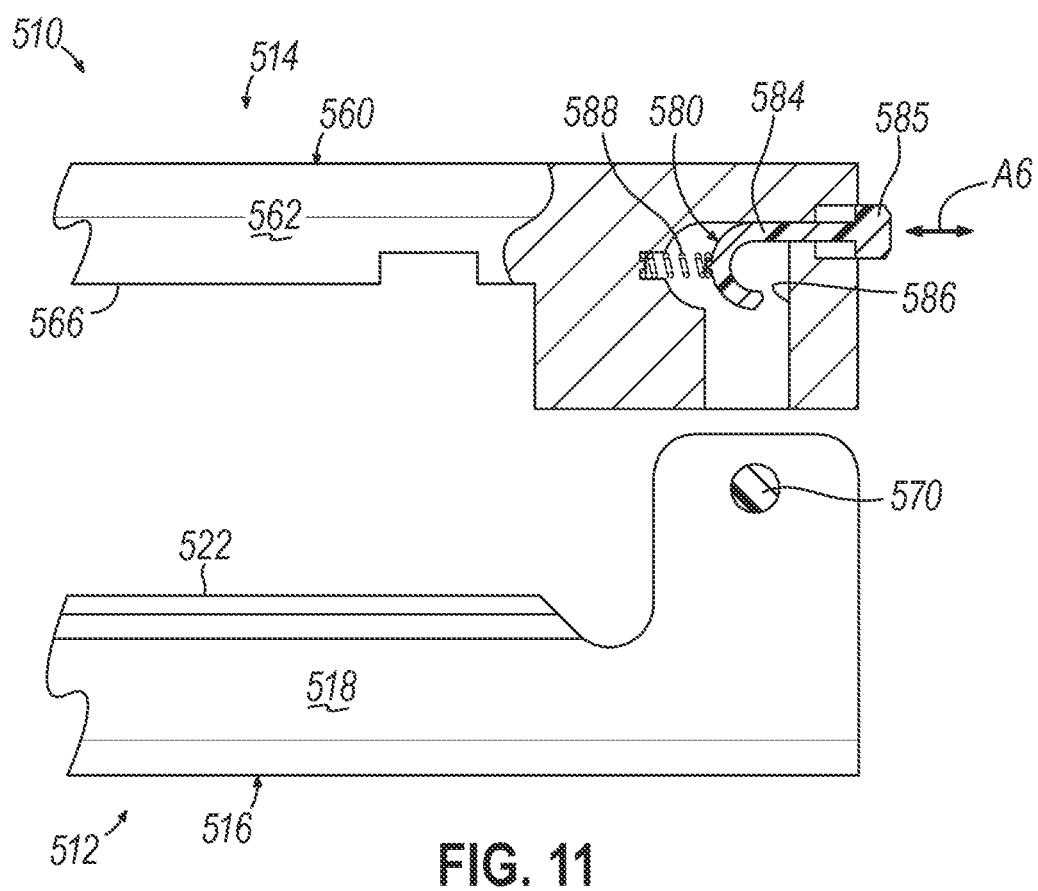
FIG. 11 depicts a partial cross sectional view of the proximal end of another exemplary linear surgical stapler having a proximally-biased translatable locking member or slide positioned on the anvil half, showing translation of the slide between locked and unlocked states capturing and releasing the proximal cartridge pin for coupling and separating the stapler halves, respectively, at their proximal ends.

D. Exemplary Linear Cutter Pin Trap Mechanism with Proximally-Biased Locking Member for Capturing Proximal Pin In some instances, it may be desirable to provide a surgical stapler having a pin trap mechanism that is proximally biased. FIG. 11 shows another exemplary surgical stapler (510) including a cartridge half (512) and an anvil half (514) that are configured in such a manner, and which are similar in structure and function to stapler (210) described above except as otherwise described below.

Cartridge half (512) includes an elongate cartridge channel (516) having a proximal frame portion (518) and a distal jaw portion (not shown). Proximal frame portion (518)

includes a laterally opposed pair of upright side flanges (522). Anvil half (514) includes an elongate anvil channel (560) having a proximal frame portion (562) and a distal jaw portion (not shown). Proximal frame portion (562) includes a laterally opposed pair of upright side flanges (566) that are configured to be received between cartridge channel side flanges (522) when anvil half (514) is coupled with cartridge half (512). A proximal pivot projection in the form of a round (e.g., circular) proximal pin (570) extends laterally between the proximal ends of cartridge channel side flanges (522).

In the example shown, anvil half (514) further includes a longitudinally translatable locking member or slide (580) having a J-shaped finger or hook portion (584) extending distally from a button (585) and configured to releasably retain proximal cartridge pin (570). Anvil half (512) also includes a cavity (586) configured to receive slide (580) and accommodate longitudinal translation of slide (580) therein between proximal locked and distal unlocked states. As shown, anvil half (514) also includes a resilient member in the form of a compression spring (588) positioned between hook portion (584) and an interior surface of cavity (586), such that spring (588) is configured to bias slide (580) proximally toward the locked state.

In this regard, hook portion (584) of slide (580) is configured to releasably and pivotably capture proximal cartridge pin (570) when in the locked state, thereby coupling the proximal ends of stapler halves (512, 514). Button (585) may be configured to permit an operator to apply a threshold distal force to slide (580) sufficient to overcome the proximal biasing of slide (580) and thereby translate slide (580) to the unlocked state such that hook portion (584) is distally withdrawn from proximal cartridge pin (570) for separating stapler halves (512, 514), as indicated by sixth arrow (A6).

Figure 12:
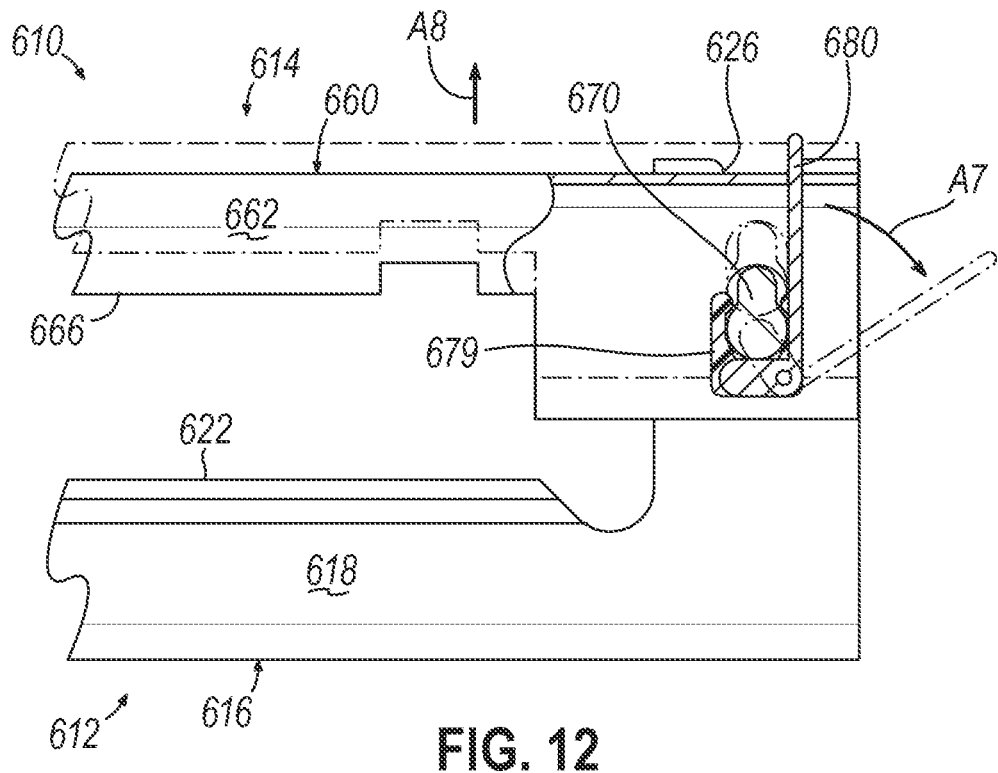
FIG. 12 depicts a partial cross sectional view of the proximal end of another exemplary linear surgical stapler having a C-clip positioned on the cartridge half with an associated ejector lever, showing rotation of the lever between locked and unlocked states allowing the proximal anvil pin to be captured by the C-clip and releasing the proximal anvil pin from the C-clip for coupling and separating the stapler halves, respectively, at their proximal ends.

E. Exemplary Linear Cutter Pin Trap Mechanism with C-Clip for Capturing Proximal Pin and Pivotable Proximal Pin Ejector Lever In some instances, it may be desirable to provide a surgical stapler having a pin trap mechanism having a pivotable ejector lever. FIG. 12 shows another exemplary surgical stapler (610) including a cartridge half (612) and an anvil half (614) that are configured in such a manner, and which are similar in structure and function to stapler (210) described above except as otherwise described below.

Cartridge half (612) includes an elongate cartridge channel (616) having a proximal frame portion (618) including a laterally opposed pair of upright side flanges (622), each including a notch (626) arranged at a proximal end thereof. Anvil half (614) includes an elongate anvil channel (660) having a proximal frame portion (662) including a laterally opposed pair of upright side flanges (666) that are configured to be received between cartridge channel side flanges (622) when anvil half (614) is coupled with cartridge half (612). A proximal pivot projection in the form of a generally pear-shaped proximal pin (670) extends laterally through the proximal ends of anvil channel side flanges (666).

In the example shown, cartridge half (612) further includes a C-clip (679) longitudinally aligned with notches (626) and configured to releasably retain proximal anvil pin (670). Cartridge half (612) also includes an L-shaped ejector lever (680) pivotably coupled to side flanges (622) slightly below and proximal relative to notches (626), such that lever (680) may be pivotable between a generally vertical locked state and a generally angled unlocked state, as indicated by seventh arrow (A7). In this regard, lever (680) is configured to urge proximal anvil pin (670) upwardly out of C-clip (679) when in the unlocked state for separating stapler halves (612, 614), as indicated by eighth arrow (A8).

While not shown, cartridge half (612) may also include a resilient member (e.g., a torsion spring) configured to bias lever (680) toward the locked state.

Figure 13:
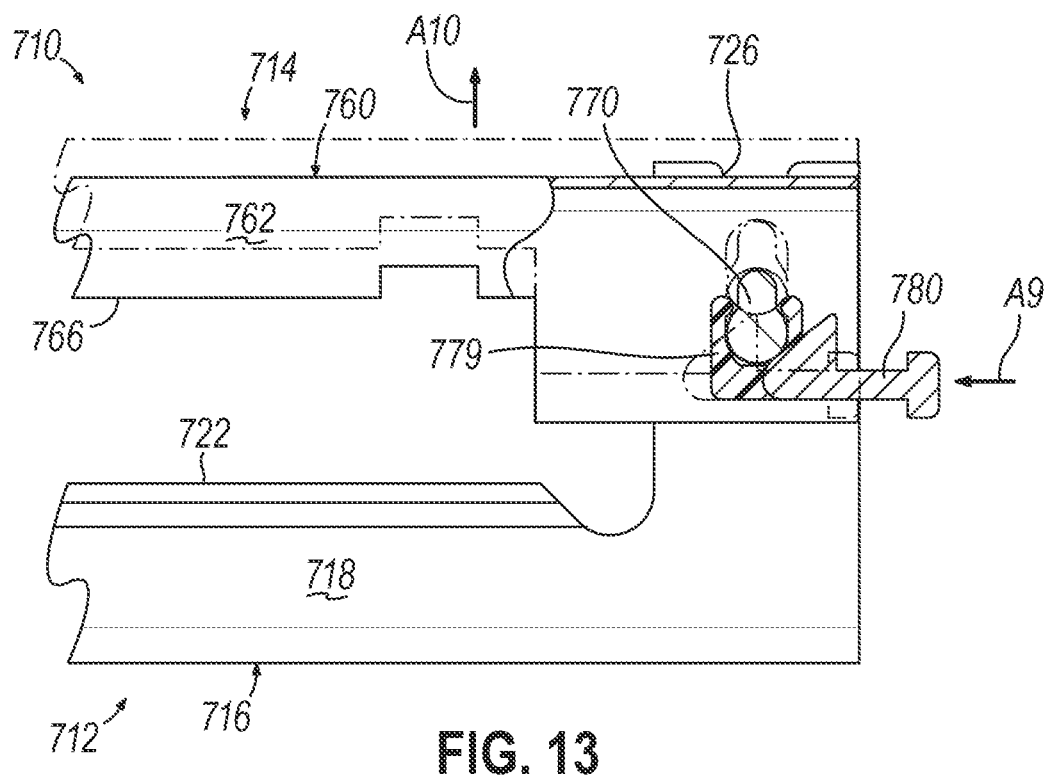
FIG. 13 depicts a partial cross sectional view of the proximal end of another exemplary linear surgical stapler having a C-clip positioned on the cartridge half with an associated ejector slide, showing translation of the slide between locked and unlocked states allowing the proximal anvil pin to be captured by the C-clip and releasing the proximal anvil pin from the C-clip for coupling and separating the stapler halves, respectively, at their proximal ends.

F. Exemplary Linear Cutter Pin Trap Mechanism with C-Clip for Capturing Proximal Pin and Slidable Proximal Pin Ejector Slide In some instances, it may be desirable to provide a surgical stapler having a pin trap mechanism having a translatable ejector slide. FIG. 13 shows another exemplary surgical stapler (710) including a cartridge half (712) and an anvil half (714) that are configured in such a manner, and which are similar in structure and function to stapler (210) described above except as otherwise described below.

Cartridge half (712) includes an elongate cartridge channel (716) having a proximal frame portion (718) including a laterally opposed pair of upright side flanges (722), each including a notch (726) arranged at a proximal end thereof. Anvil half (714) includes an elongate anvil channel (760) having a proximal frame portion (762) including a laterally opposed pair of upright side flanges (766) that are configured to be received between cartridge channel side flanges (722) when anvil half (714) is coupled with cartridge half (712). A proximal pivot projection in the form of a generally pear-shaped proximal pin (770) extends laterally through the proximal ends of anvil channel side flanges (766).

In the example shown, cartridge half (712) further includes a C-clip (779) longitudinally aligned with notches (726) and configured to releasably retain proximal anvil pin (770). Cartridge half (712) also includes a J-shaped ejector slide (780) slidably coupled to side flanges (722) slightly below and proximal relative to notches (726), such that slide (780) may be translatable between a proximal locked state and a distal unlocked state, as indicated by ninth arrow (A9). In this regard, slide (780) is configured to urge proximal anvil pin (770) upwardly out of C-clip (779) when in the unlocked state for separating stapler halves (712, 714), as indicated by tenth arrow (A10).

While not shown, cartridge half (712) may also include a resilient member (e.g., a compression spring) configured to bias slide (780) toward the locked state.

Figure 14A:
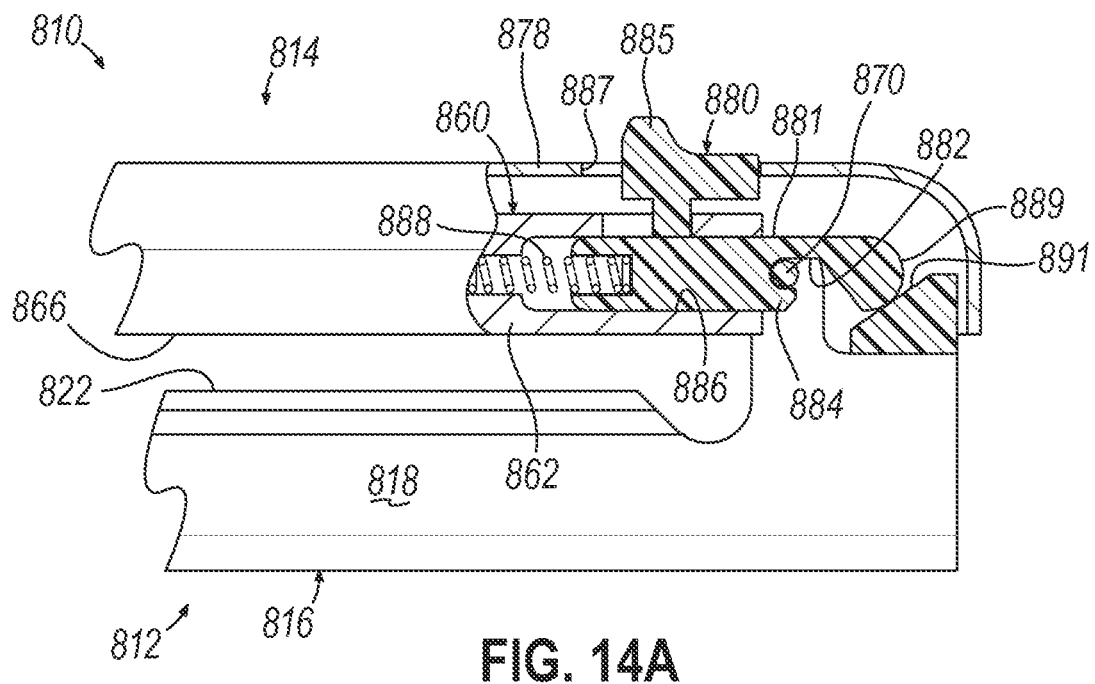
FIG. 14A depicts a partial cross sectional view of the proximal end of another exemplary linear surgical stapler having a proximally-biased translatable locking member or slide with a camming release surface positioned on the anvil half, showing the slide in a locked state capturing the proximal cartridge pin for coupling the stapler halves at their proximal ends.
Figure 14B:
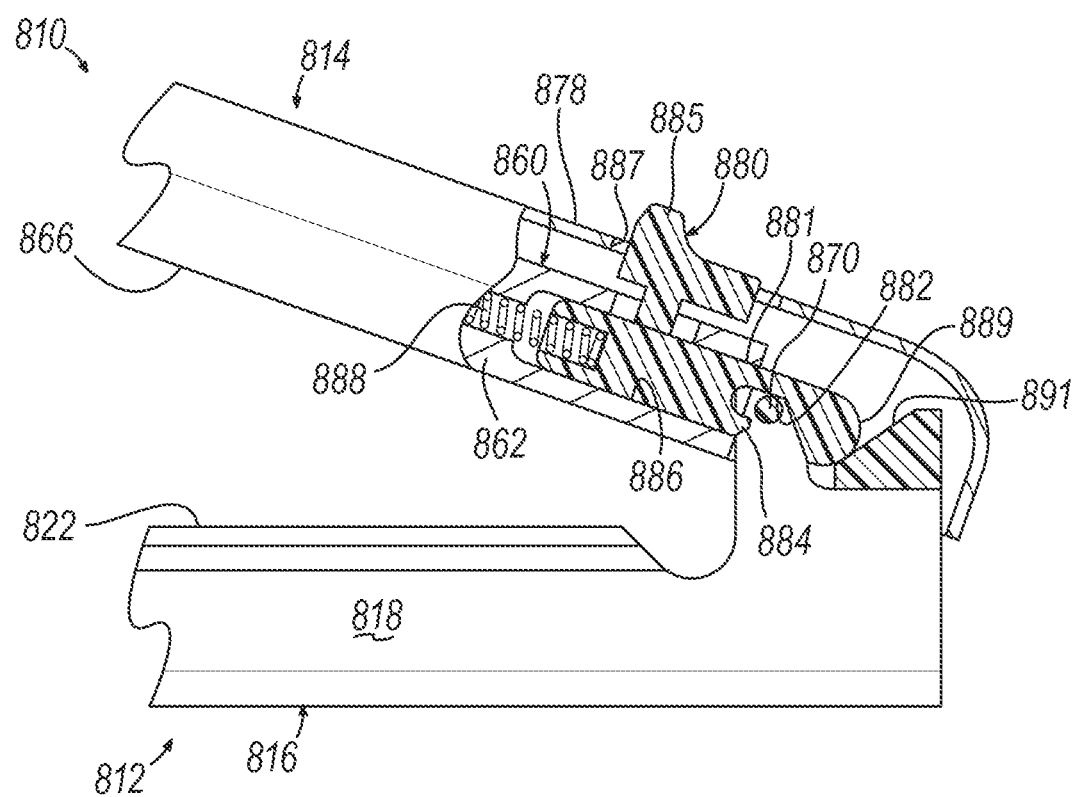
FIG. 14B depicts a partial cross sectional view of the proximal end of the linear surgical stapler of FIG. 14A, showing the slide in an unlocked state releasing the proximal cartridge pin for separating the stapler halves.

G. Exemplary Linear Cutter Pin Trap Mechanism with Proximally-Biased Locking Member for Capturing Proximal Pin and Camming Release Surfaces In some instances, it may be desirable to provide a surgical stapler having a pin trap mechanism that is proximally biased and having camming release features. FIGS. 14A-14B show another exemplary surgical stapler (810) including a cartridge half (812) and an anvil half (814) that are configured in such a manner, and which are similar in structure and function to stapler (210) described above except as otherwise described below.

Cartridge half (812) includes an elongate cartridge channel (816) having a proximal frame portion (818) including a laterally opposed pair of upright side flanges (822). Anvil half (814) includes an elongate anvil channel (860) having a proximal frame portion (862) including a laterally opposed pair of upright side flanges (866) that are configured to be received between cartridge channel side flanges (822) when anvil half (814) is coupled with cartridge half (812). A proximal pivot projection in the form of a round (e.g., circular) proximal pin (870) extends laterally between the proximal ends of cartridge channel side flanges (822). Additionally, an anvil shroud (878) is affixed to and covers an outwardly facing side of anvil channel (860).

In the example shown, anvil half (814) further includes a longitudinally translatable locking member or slide (880) having a base portion (881) including a stepped notch (882) defining a hook portion (884). More particularly, notch (882) includes a generally downwardly-facing open end and a generally proximally-facing closed end configured to releasably retain proximal cartridge pin (870). In the example shown, slide (880) further includes a button (885) extending upwardly from base (881) and configured to assist an operator with gripping and manipulating slide (880). The illustrated slide (880) also includes a generally convex proximal camming surface (889).

Anvil half (812) also includes a cavity (886) configured to receive slide (880) and accommodate longitudinal translation of slide (880) therein between a proximal locked state, as shown in FIG. 14A, and a distal unlocked state, as shown in FIG. 14B. As shown, anvil shroud (878) includes an aperture (887) configured to permit button (885) to extend upwardly therethrough and accommodate longitudinal translation thereof corresponding to translation of slide (880) between the locked and unlocked states. As shown, anvil half (814) also includes a resilient member in the form of a compression spring (888) positioned between base (881) and an interior surface of cavity (886), such that spring (888) is configured to bias slide (880) proximally toward the locked state.

In this regard, the closed end of notch (882) of slide (880) is configured to releasably and pivotably capture proximal cartridge pin (870) when in the locked state, thereby coupling the proximal ends of stapler halves (812, 814). Button (885) may be configured to permit an operator to apply a threshold distal force to slide (880) sufficient to overcome the proximal biasing of slide (880) and thereby translate slide (880) to the unlocked state such that the closed end of notch (882) is distally withdrawn from proximal cartridge pin (870) for separating stapler halves (812, 814). In addition or alternatively, camming surface (889) of slide (880) may be configured to interact with a corresponding angled camming surface (891) positioned on cartridge half (812) to urge slide (880) distally in response to a threshold separation force being applied at the proximal ends of stapler halves (812, 814), such as via rotation of anvil half (814) away from cartridge half (812). For example, camming surfaces (889, 891) may be configured to urge slide (880) to the unlocked state in response to rotation of anvil half (814) away from cartridge half (812) to a predetermined maximum orientation for decoupling of stapler halves (812, 814).

Figure 15A:
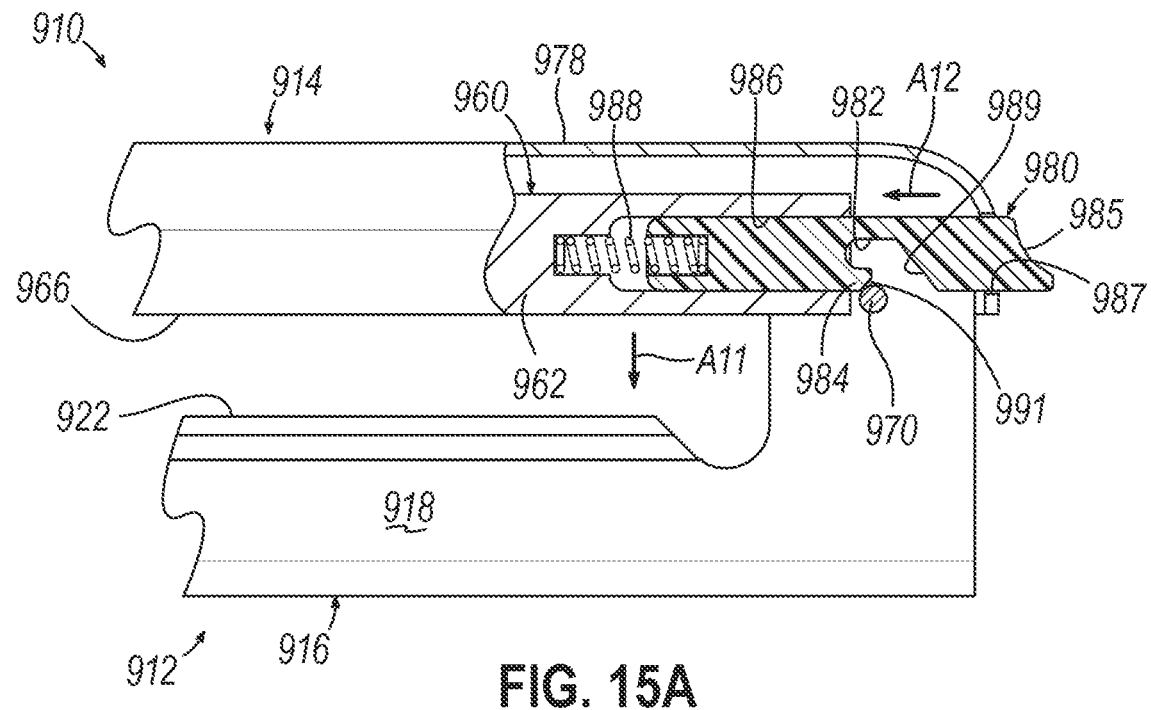
FIG. 15A depicts a partial cross sectional view of the proximal end of another exemplary linear surgical stapler having a proximally-biased translatable locking member or slide with camming insertion and separation surfaces positioned on the anvil half, showing the camming insertion surface of the slide interacting with the proximal cartridge pin to translate the slide distally during approximation of the stapler halves.
Figure 15B:
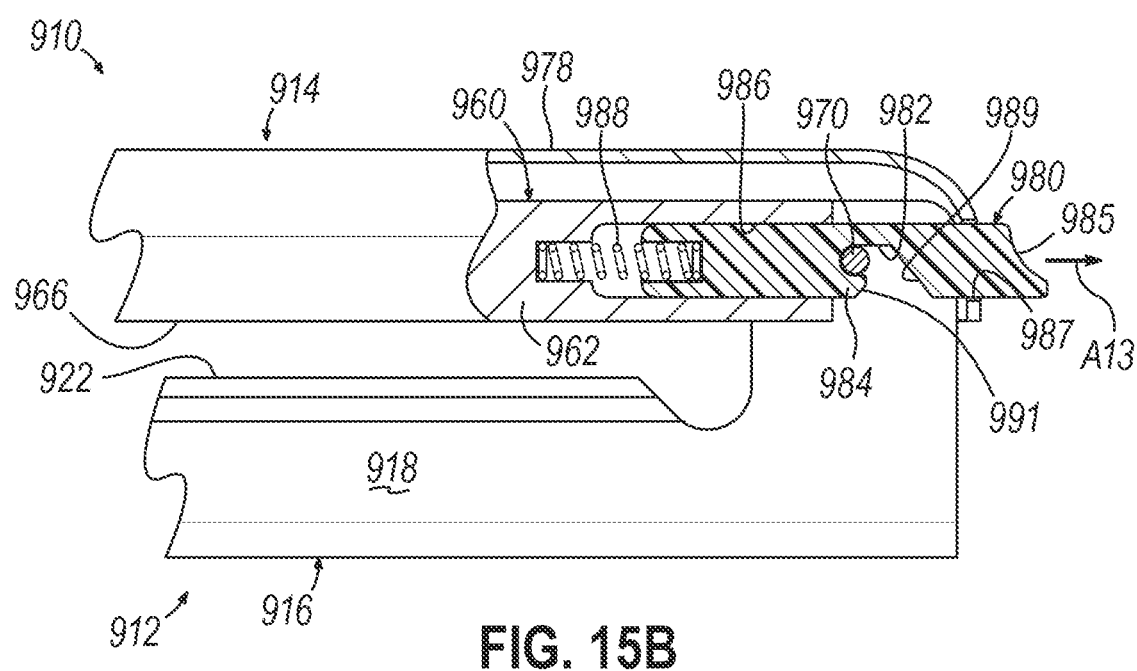
FIG. 15B depicts a partial cross sectional view of the proximal end of the linear surgical stapler of FIG. 15A, showing the slide in a locked state capturing the proximal cartridge pin for coupling the stapler halves at their proximal ends.
Figure 15C:
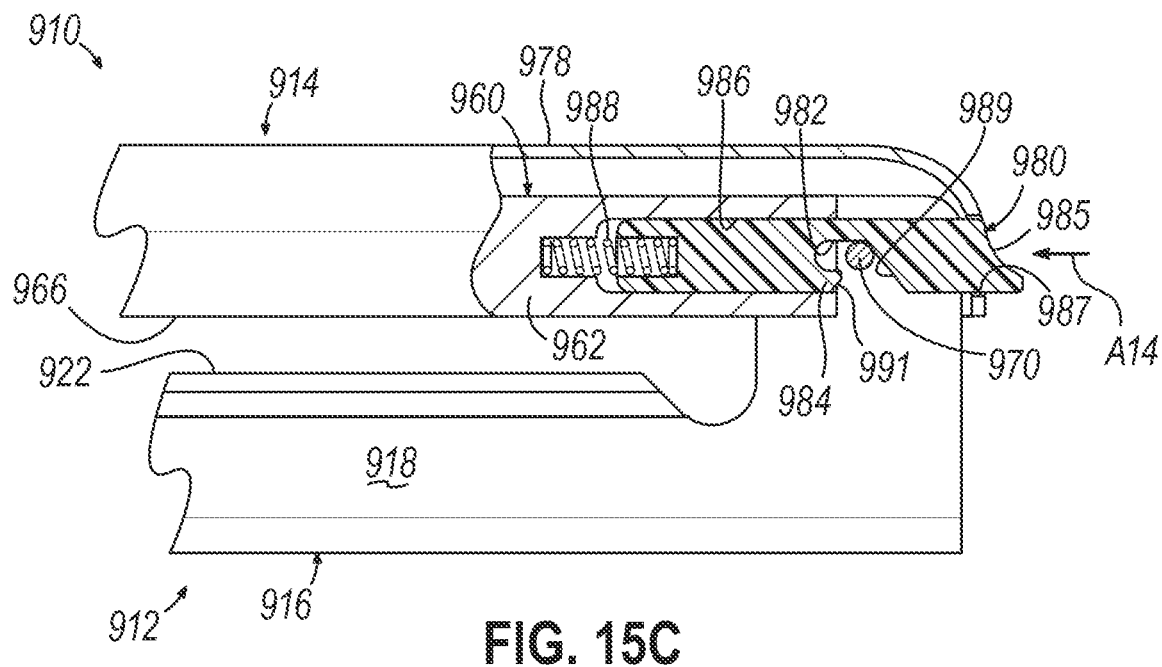
FIG. 15C depicts a partial cross sectional view of the proximal end of the linear surgical stapler of FIG. 15A, showing the slide in an unlocked state releasing the proximal cartridge pin for separating the stapler halves, and further showing the camming separation surface of the slide interacting with the proximal cartridge pin to assist in separating the proximal ends of the stapler halves.

H. Exemplary Linear Cutter Pin Trap Mechanism with Proximally-Biased Locking Member for Capturing Proximal Pin and Camming Separation Surfaces In some instances, it may be desirable to provide a surgical stapler having a pin trap mechanism that is proximally biased and having camming separation features. FIGS. 15A-15C show another exemplary surgical stapler (910) including a cartridge half (912) and an anvil half (914) that are configured in such a manner, and which are similar in structure and function to stapler (210) described above except as otherwise described below.

Cartridge half (912) includes an elongate cartridge channel (916) having a proximal frame portion (918) including a laterally opposed pair of upright side flanges (922). Anvil half (914) includes an elongate anvil channel (960) having a proximal frame portion (962) including a laterally opposed pair of upright side flanges (966) that are configured to be received between cartridge channel side flanges (922) when anvil half (914) is coupled with cartridge half (912). A proximal pivot projection in the form of a round (e.g., circular) proximal pin (970) extends laterally between the proximal ends of cartridge channel side flanges (922). Additionally, an anvil shroud (978) is affixed to and covers an outwardly facing side of anvil channel (960).

In the example shown, anvil half (914) further includes a longitudinally translatable locking member or slide (980) including a stepped notch (982) defining a hook portion (984). More particularly, notch (982) includes a generally downwardly-facing open end and a generally proximally-facing closed end configured to releasably retain proximal cartridge pin (970). In the example shown, slide (980) further includes a proximal button surface (985) configured to assist an operator with gripping and manipulating slide (980). The illustrated slide (980) also includes generally angled proximal and distal camming surfaces (989, 991) defined by notch (982). More particularly, proximal camming surface (989) is inclined distally in an upward direction from a proximal lower edge of notch (982), and distal camming surface (991) is inclined proximally in an upward direction from a distal lower edge of notch (982) (e.g., along a proximal end of hook portion (984)).

Anvil half (914) also includes a cavity (986) configured to receive slide (980) and accommodate longitudinal translation of slide (980) therein between a proximal locked state, as shown in FIG. 15B, and a distal unlocked state, as shown in FIG. 15C. As shown, anvil shroud (978) includes an aperture (987) configured to permit button surface (985) to extend proximally therethrough for allowing an operator to access button surface (985). In the example shown, button surface (985) and aperture (987) are both positioned at a proximal end of anvil half (914) with button surface (985) facing proximally, such that button surface (985) may be accessible via aperture (987) irrespective of whether a clamp lever (not shown) of stapler (910) is in an open or closed position. For example, button surface (985) and aperture (987) may remain unobstructed by the clamp lever when the clamp lever is in a closed position in which a proximal end of the clamp lever confronts cartridge channel frame portion (918). As shown, anvil half (914) also includes a resilient member in the form of a compression spring (988) positioned between slide (980) and an interior surface of cavity (986), such that spring (988) is configured to bias slide (880) proximally toward the locked state.

In this regard, the closed end of notch (982) of slide (980) is configured to releasably and pivotably capture proximal cartridge pin (970) when in the locked state, thereby coupling the proximal ends of stapler halves (912, 914). Distal camming surface (991) of slide (980) may be configured to interact with proximal cartridge pin (970) to initially urge slide (980) distally during coupling of stapler halves (912, 914), as indicated by eleventh and twelfth arrows (A11, A12) in FIG. 15A, and spring (988) may be configured to subsequently bias slide (880) toward the locked state to seat proximal cartridge pin (970) at the closed end of notch (982), as indicated by thirteenth arrow (A13) in FIG. 15B. Button surface (985) may be configured to permit an operator to apply a threshold distal force to slide (980) sufficient to overcome the proximal biasing of slide (980) and thereby translate slide (980) to the unlocked state such that the closed end of notch (982) is distally withdrawn from proximal cartridge pin (970) for separating stapler halves (912, 914). In addition or alternatively, proximal camming surface (989) of slide (980) may be configured to interact with proximal cartridge pin (970) to urge the proximal end of anvil half (914) upwardly away from the proximal end of cartridge half (912) during translation of slide (980) toward the unlocked state to thereby separate stapler halves (912, 914), as indicated by fourteenth arrow (A14) in FIG. 15C.

Though not shown, an opposite configuration of proximal pin (970) and slide (980) may be provided in which proximal pin (970) is provided on anvil half (912) and slide (980) is provided on cartridge half (914).

During operation, the operator may initially couple stapler halves (912, 914) together at their proximal ends by lowering anvil half (914) toward cartridge half (912) such that distal camming surface (991) and proximal cartridge pin (970) cooperate to urge slide (980) distally and allow proximal cartridge pin (970) to enter notch (982), and spring (988) may subsequently bias slide (880) toward the locked state to seat proximal cartridge pin (970) at the closed end of notch (982). The operator may then rotate anvil half (914) relative to cartridge half (912) about proximal cartridge pin (970) as desired, such as between open and clamped states, while stapler halves (912, 914) remain reliably coupled to each other to perform a cutting and/or stapling procedure. If desired, the operator may selectively separate stapler halves (912, 914) from each other by translating slide (980) to the unlocked state to thereby release proximal cartridge pin (970) from the closed end of notch (982) and such that proximal camming surface (989) and proximal cartridge pin (970) cooperate to urge the proximal end of anvil half (914) upwardly away from the proximal end of cartridge half (912).

Figure 16:
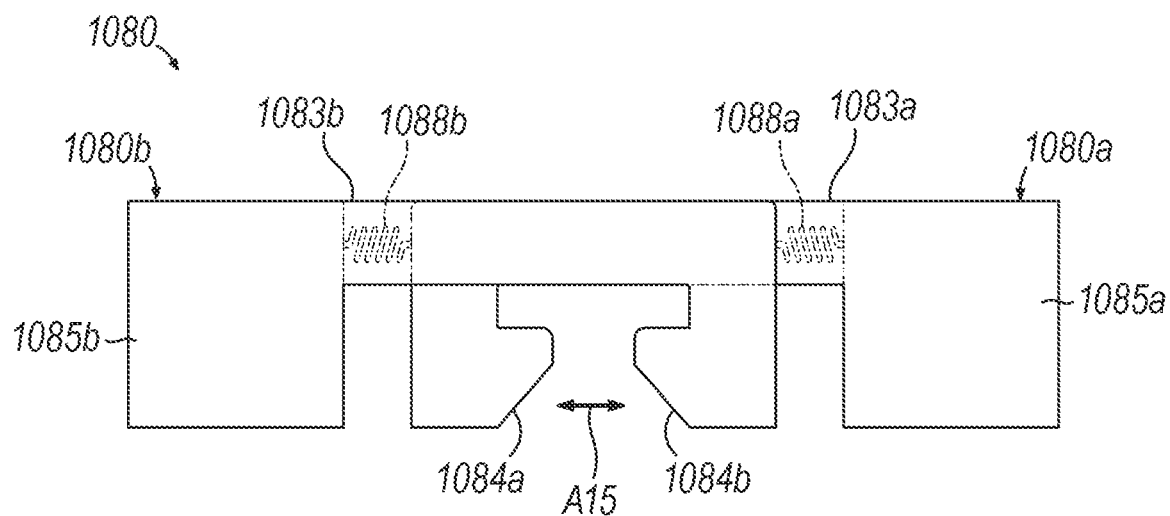
FIG. 16 depicts a cross sectional view of another exemplary locking member for a linear surgical stapler having a longitudinally-outwardly biased pair of translatable slides.

I. Exemplary Linear Cutter Pin Trap Mechanism with Opposing Biased Locking Member Portions for Capturing Proximal Pin In some instances, it may be desirable to provide a pin trap mechanism for a surgical stapler having a longitudinally opposed pair of slides. FIG. 16 shows an exemplary locking member (1080) that is configured in such a manner, and which may be incorporated into a stapler similar in structure and function to stapler (210) described above except as otherwise described below.

Locking member (1080) includes a longitudinally opposed pair of longitudinally translatable proximal and distal slides (1080a, 1080b). In the example shown, slides (1080a, 1080b) each include a longitudinal arm (1083a, 1083b) and a longitudinally-inward finger or hook portion (1084a, 1084b) configured to cooperate with each other to releasably retain a proximal pivot projection (e.g., a proximal anvil pin or a proximal cartridge pin) of the stapler. More particularly, hook portion (1084a) of proximal slide (1080a) extends laterally inwardly from a distal end of arm (1083a), and hook portion (1084b) of distal slide (1080b) extends laterally inwardly from a proximal end of arm (1083b). In the example shown, slides (1080a, 1080b) each further include a longitudinally-outward button (1085a, 1085b) configured to assist an operator with gripping and manipulating the respective slide (1080a, 1080b). Slides (1080a, 1080b) may be configured to be received by one or more cavities provided in a cartridge half or an anvil half of the stapler to accommodate longitudinal translation of slides (1080a, 1080b) therein relative to each other between a longitudinally outward locked state and a longitudinally inward unlocked state, as indicated by fifteenth arrow (A15). In one example, such a cartridge half or anvil half may further include an aperture (e.g., in a shroud thereof) configured to permit buttons (1085a, 1085b) to extend outwardly therethrough and accommodate longitudinal translation thereof corresponding to translation of the respective slides (1080a, 1080b) between the locked and unlocked states. As shown, locking member (1080) also includes a longitudinally opposed pair of resilient members in the form of proximal and distal compression springs (1088a, 1088b) positioned between slides (1080a, 1080b), such that springs (1088a, 1088b) are configured to bias slides (1080a, 1080b) longitudinally outwardly relative to each other toward the locked state.

In this regard, hook portions (1084a, 1084b) of slides (1080a, 1080b) are configured to cooperate with each other to releasably and pivotably capture the proximal pivot projection of the stapler when in the locked state, thereby coupling the proximal ends of the stapler halves. Buttons (1085a, 1085b) may be configured to permit an operator to apply threshold longitudinally-inward forces to slides (1080a, 1080b) sufficient to overcome the longitudinally-outward biasing of slides (1080a, 1080b) and thereby translate slides (1080a, 1080b) to the unlocked state such that hook portions (1085a, 1085b) are longitudinally withdrawn from the proximal pivot projection for separating the stapler halves. In addition or alternatively, hook portions (1085a, 1085b) may include angled or rounded camming surfaces (not shown) configured to interact with the proximal pivot projection to urge slides (1080a, 1080b) longitudinally inwardly in response to a threshold separation force being applied at the proximal ends of the stapler halves, such as via rotation of the stapler halves away from each other. For example, such camming surfaces may be configured to urge slides (1080a, 1080b) to the unlocked state in response to rotation of the stapler halves away from each other to a predetermined maximum orientation for decoupling of the stapler halves.

Figure 17A:
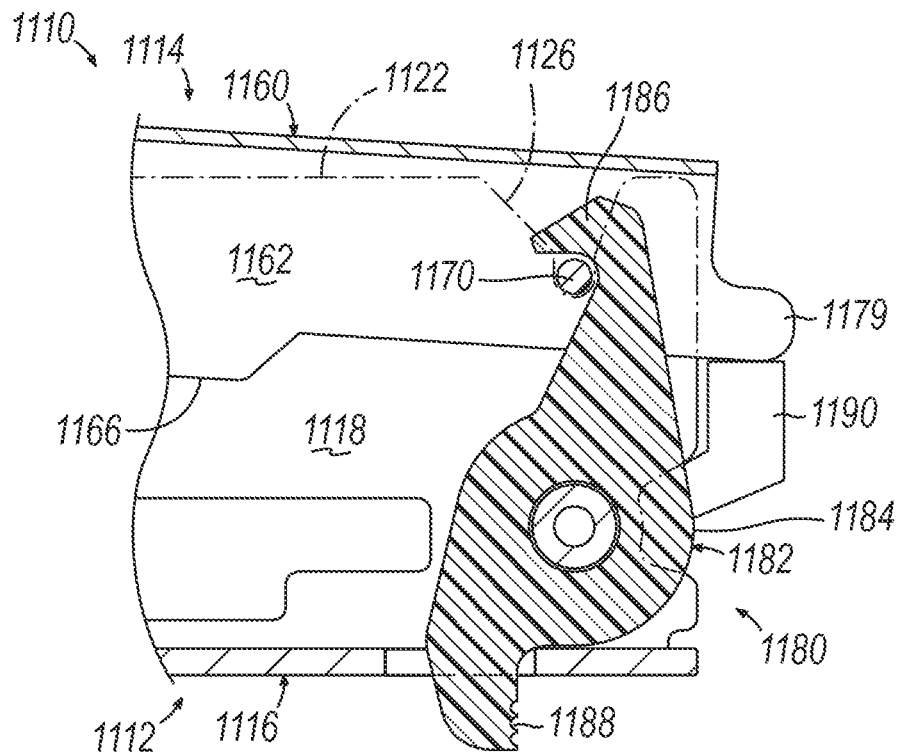
FIG. 17A depicts a cross sectional view of the proximal end of another exemplary linear surgical stapler having a rotatable locking member, showing the locking member in a locked state capturing the proximal anvil pin for coupling the stapler halves at their proximal ends.
Figure 17B:
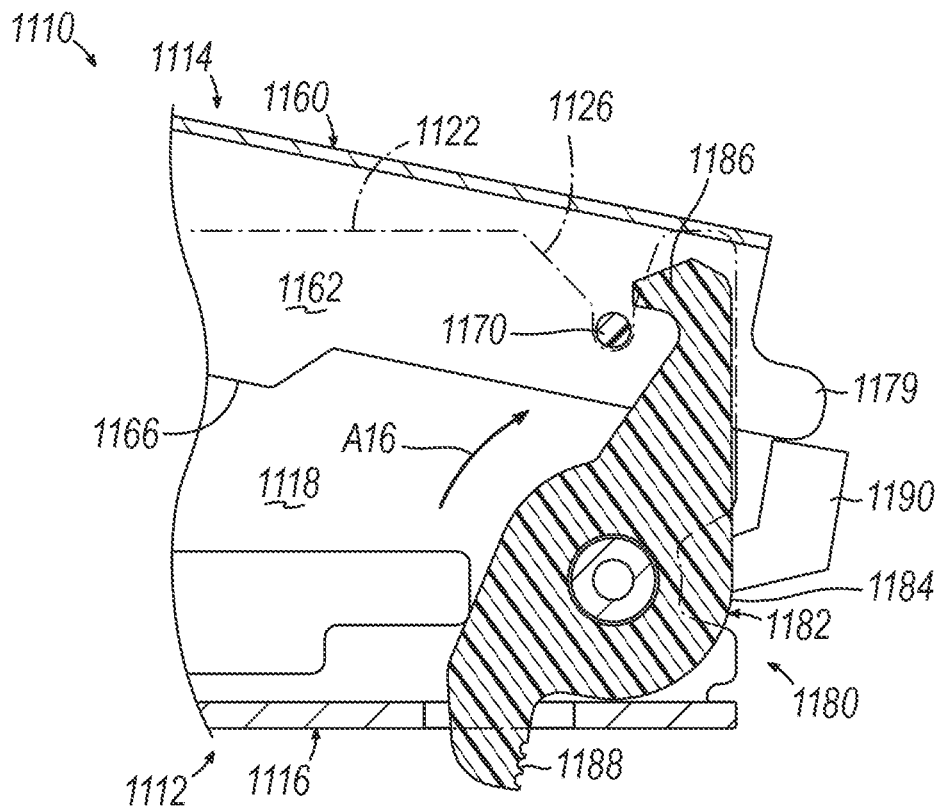
FIG. 17B depicts a cross sectional view of the proximal end of the linear surgical stapler of FIG. 17A, showing rotation of the locking member to an unlocked state releasing the proximal cartridge pin for separating the stapler halves in response to the anvil half of the stapler being pivoted open relative to the cartridge half.

J. Exemplary Linear Cutter Pin Trap Mechanism with Rotatable Locking Member for Capturing Proximal Pin and Torque Ami Feature In some instances, it may be desirable to provide a surgical stapler having a pin trap mechanism that is rotatable and has torque arm release features. FIGS. 17A-17B show another exemplary surgical stapler (1110) including a cartridge half (1112) and an anvil half (1114) that are configured in such a manner, and which are similar in structure and function to stapler (210) described above except as otherwise described below.

Cartridge half (1112) includes an elongate cartridge channel (1116) having a proximal frame portion (1118) including a laterally opposed pair of upright side flanges (1122), each including a tapered notch (1126) arranged at a proximal end thereof. Anvil half (1114) includes an elongate anvil channel (1160) having a proximal frame portion (1162) including a laterally opposed pair of upright side flanges (1166) that are configured to be received between cartridge channel side flanges (1122) when anvil half (1114) is coupled with cartridge half (1112). A proximal pivot projection in the form of a round (e.g., circular) proximal pin (1170) extends laterally between the proximal ends of anvil channel side flanges (1166). Additionally, anvil half (1114) includes a proximal anvil channel extension (1179) projecting proximally from a proximal end of anvil channel (1160).

In the example shown, proximal frame portion (1118) of cartridge channel (1116) supports a proximal retaining assembly (1180) generally similar to those described in U.S. Pub. No. 2020/0046351, entitled "Decoupling Mechanism for Linear Surgical Stapler," published on Feb. 13, 2020, issued as U.S. Pat. No. 11,033,266 on Jun. 15, 2021, the disclosure of which is incorporated by reference herein. An anvil latch member (1182) of proximal retaining assembly (1180) includes a generally cylindrical body (1184), a latch finger (1186) extending upwardly from body (1184), a release button (1188) extending downwardly from body (1184), and a torque arm (1190) extending proximally and laterally outwardly from body (1184).

As shown in FIG. 17A, anvil half (1114) is configured to be pivoted open relative to cartridge half (1112) through a first range of motion about a first pivot axis defined by proximal anvil pin (1170) to a predetermined degree at which proximal anvil channel extension (1179) directly contacts an upper surface of torque arm (1190). As shown in FIG. 17B, pivoting anvil half (1114) further open through a second range of motion about proximal anvil pin (1170) causes proximal anvil channel extension (1179) to drive torque arm (1190) downwardly, as indicated by sixteenth arrow (A16). This downward motion of torque arm (1190) causes anvil latch member (1182) to rotate such that latch finger (1186) moves proximally to release proximal anvil pin (1170). Accordingly, torque arm (1190) and proximal anvil channel extension (1179) cooperate to define a decoupling mechanism that is similar in function to those described in U.S. Pub. No. 2020/0046351, issued as U.S. Pat. No. 11,033,266 on Jun. 15, 2021, incorporated by reference above. In that regard, further opening of anvil half (1114) causes anvil half (1114) to pivot relative to cartridge half (1112) about a second pivot axis defined by the point of contact between torque arm (1190) and proximal anvil channel extension (1179). This second pivot axis of the decoupling mechanism is located proximal to the first pivot axis defined by proximal anvil pin (1170). Pivoting anvil half (1114) about this second pivot axis lifts proximal anvil pin (1170) from proximal notches (1126) of cartridge half (1112) while latch member (1182) remains in the release position, such that the proximal ends of stapler halves (1112, 1114) may be separated from one another.

In some such versions, the modified anvil latch member (1182) of linear surgical stapler (1110) may be suitably resiliently biased toward its distal latching position to resist a predetermined amount of torque applied by proximal anvil channel extension (1179) via torque arm (1190). This may enable a user to hold stapler (1110) in an open configuration in which stapler halves (1112, 1114) are pivotably opened to the point that proximal anvil channel extension (1179) rests upon torque arm (1190) of anvil latch member (1182). Simultaneously, anvil latch member (1182) maintains its distal latching position to prevent decoupling of the proximal ends of stapler halves (1112, 1114) until the user actively forces anvil half (1114) further open relative to cartridge half (1112).

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a first stapler half including an anvil surface having a plurality of staple forming pockets; (b) a second stapler half configured to releasably couple with the first stapler half, wherein the second stapler half is operable to deploy staples toward the anvil surface; (c) a proximal pivot projection positioned on one of the first or second stapler halves and extending laterally relative to a longitudinal axis of the surgical stapler, wherein the first and second stapler halves are configured to pivot relative to each other about the proximal pivot projection; and (d) a locking member positioned on the other of the first or second stapler halves, wherein the locking member is configured to translate along the longitudinal axis of the surgical stapler between a proximal locked state in which the locking member selectively captures the proximal pivot projection and a distal unlocked state in which the locking member selectively releases the proximal pivot projection, wherein the locking member is biased proximally toward the locked state.

Example 2

The surgical stapler of Example 1, wherein the locking member includes a notch having a proximally-facing closed end configured to pivotably receive the proximal pivot projection when in the locked state.

Example 3

The surgical stapler of Example 2, wherein the notch defines a camming surface configured to selectively engage the proximal pivot projection in response to translation of the locking member toward the unlocked state to urge the first and second stapler halves away from each other.

Example 4

The surgical stapler of Example 3, wherein the camming surface is inclined distally in a direction away from the second stapler half from a proximal lower edge of the notch.

Example 5

The surgical stapler of any one or more of Examples 2 through 4, wherein the notch defines a camming surface configured to selectively engage the proximal pivot projection in response to linear approximation of the first stapler half toward the second stapler half to translate the locking member toward the unlocked state.

Example 6

The surgical stapler of Example 5, wherein the camming surface is inclined proximally in a direction away from the second stapler half from a distal lower edge of the notch.

Example 7

The surgical stapler of any of the preceding Examples, wherein the locking member includes a button portion configured to receive a threshold longitudinal force sufficient to overcome the proximal biasing of the locking member for translating the locking member distally toward the unlocked state.

Example 8

The surgical stapler of Example 7, wherein the other of the first or second stapler halves includes an aperture, wherein the button portion extends proximally through the aperture.

Example 9

The surgical stapler of any of the preceding Examples, further comprising a resilient member configured to bias the locking member proximally toward the locked state.

Example 10

The surgical stapler of Example 9, wherein the resilient member includes at least one of a torsion spring, an extension spring, or a compression spring.

Example 11

The surgical stapler of any of the preceding Examples, wherein the locking member is configured to continuously capture the proximal pivot projection while in the locked state during pivoting of the first stapler half relative to the second stapler half about the proximal pivot projection between a clamped state of the surgical stapler and an open state of the surgical stapler in which proximal ends of the first and second stapler halves remain releasably coupled together.

Example 12

The surgical stapler of any of the preceding Examples, wherein the proximal pivot projection is positioned on the second stapler half and the locking member is positioned on the first stapler half.

Example 13

The surgical stapler of any one or more of Examples 1 through 11, wherein the proximal pivot projection is positioned on the first stapler half and the locking member is positioned on the second stapler half.

Example 14

The surgical stapler of any of the preceding Examples, wherein the proximal pivot projection includes a pin having a circular cross sectional shape.

Example 15

The surgical stapler of any of the preceding Examples, wherein the second stapler half includes an elongate member having a distal portion configured to receive a staple cartridge.

Example 16

A surgical stapler comprising: (a) a first stapler half including an anvil surface having a plurality of staple forming pockets; (b) a second stapler half configured to releasably couple with the first stapler half, wherein the second stapler half is operable to deploy staples toward the anvil surface; (c) a proximal pivot projection positioned on one of the first or second stapler halves and extending laterally relative to a longitudinal axis of the surgical stapler, wherein the first and second stapler halves are configured to pivot relative to each other about the proximal pivot projection; and (d) a slide positioned on the other of the first or second stapler halves, wherein the slide is configured to translate along the longitudinal axis of the surgical stapler between a locked state and an unlocked state, wherein the slide comprises: (i) a hook portion configured to selectively capture and release the proximal pivot projection when the slide is in the latched and unlatched states, respectively, and (ii) a first camming surface configured to selectively engage the proximal pivot projection in response to translation of the slide toward the unlocked state to urge the first and second stapler halves away from each other.

Example 17

The surgical stapler of Example 16, wherein the slide further includes a second camming surface configured to selectively engage the proximal pivot projection in response to linear approximation of the first stapler half toward the second stapler half to translate the slide toward the unlocked state.

Example 18

A surgical stapler comprising: (a) a first stapler half comprising: (i) an anvil surface having a plurality of staple forming pockets, and (ii) a proximal pivot projection extending laterally relative to a longitudinal axis of the surgical stapler, wherein the proximal pivot projection has a non-circular transverse cross-section; and (b) a second stapler half configured to releasably couple with the first stapler half and to pivot relative thereto about the proximal pivot projection, wherein the second stapler half comprises: (i) an elongate member having a distal portion operable to deploy staples toward the anvil surface and at least one proximal notch configured to pivotably receive the proximal pivot projection of the first stapler half, and (ii) a locking member configured to translate along the longitudinal axis of the surgical stapler between a distal locked state in which the locking member selectively captures the proximal pivot projection and a proximal unlocked state in which the locking member selectively releases the proximal pivot projection for coupling and separating the first and second stapler halves, respectively, wherein a portion of the proximal pivot projection is configured to selectively frictionally engage at least one of a proximal surface of the at least one proximal notch or a distal surface of the locking member in response to rotation of the first stapler half away from the second stapler half about the proximal pivot projection to an open state in which the first and second stapler halves assume a predetermined maximum angular orientation relative to one another and remain releasably coupled together at their proximal ends.

Example 19

The surgical stapler of Example 18, wherein the locking member includes a hook portion configured to sandwich the proximal pivot projection against a closed end of the at least one proximal notch when in the locked state.

Example 20

The surgical stapler of Example 19, wherein the hook portion is configured to continuously confront the proximal pivot projection while in the locked state during pivoting of the first stapler half relative to the second stapler half about the proximal pivot projection between a clamped state of the surgical stapler and the open state of the surgical stapler.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. Pat. No. 10,631,866, entitled "Release Mechanism for Linear Surgical Stapler," issued on Apr. 28, 2020; U.S. Pub. No. 2019/0239882, entitled "Lockout Assembly for Linear Surgical Stapler," published on Aug. 8, 2019, issued as U.S. Pat. No. 10,667,818 on Jun. 2, 2020; U.S. Pub. No. 2019/0239886, entitled "Features to Align and Close Linear Surgical Stapler", published on Aug. 8, 2019, issued as U.S. Pat. No. 10,932,781 on Mar. 2, 2021; U.S. Pub. No. 2019/0239883, entitled "Releasable Coupling Features for Proximal Portions of Linear Surgical Stapler," published on Aug. 8, 2019, issued as U.S. Pat. No. 10,898,197 on Jan. 26, 2021; U.S. Pub. No. 2019/0239884, entitled "Firing Lever Assembly for Linear Surgical Stapler," published on Aug. 8, 2019, issued as U.S. Pat. No. 10,874,398 on Dec. 29, 2020; U.S. Pub. No. 2019/0239885, entitled "Clamping Mechanism for Linear Surgical Stapler," published on Aug. 8, 2019, issued as U.S. Pat. No. 10,687,819 on Jun. 23, 2020; U.S. Pub. No. 2020/0046350, entitled "Firing System for Linear Surgical Stapler," published on Feb. 13, 2020, issued as U.S. Pat. No. 10,898,187 on Jan. 26, 2021; U.S. Pub. No. 2020/0046353, entitled "Clamping Assembly for Linear Surgical Stapler," published on Feb. 13, 2020; issued as U.S. Pat. No. 11,278,285 on Mar. 22, 2022; U.S. Pub. No. 2020/0113561, entitled "Anvil Assembly for Linear Surgical Stapler," published on Apr. 16, 2020, issued as U.S. Pat. No. 11,045,193 on Jun. 29, 2021; U.S. Pub. No. 2020/0113562, entitled "Closure Assembly for Linear Surgical Stapler," published on Apr. 16, 2020, issued as U.S. Pat. No. 10,905,419 on Feb. 2, 2021; and/or U.S. Pub. No. 2020/0046351, entitled "Decoupling Mechanism for Linear Surgical Stapler," published on Feb. 13, 2020, issued as U.S. Pat. No. 11,033,266 on Jun. 15, 2021. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. application Ser. No. 16/886,919, entitled "Surgical Linear Cutter Wishbone Separation Mechanism with Detent," filed on May 29, 2020 and issued as U.S. Pat. No. 11,224,425 on Jan. 18, 2022; and/or U.S. application Ser. No. 16/886,924, entitled "Separation Mechanism for Surgical Linear Cutter," filed on May 29, 2020 and published as U.S. Pub. No. 2021/0369272 on Dec. 2, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical stapler comprising:
   (a) a first stapler half including an anvil surface having a plurality of staple forming pockets;
   (b) a second stapler half configured to releasably couple with the first stapler half, wherein the second stapler half is operable to deploy staples toward the anvil surface;
   (c) a proximal pivot projection positioned on one of the first or second stapler halves and extending laterally relative to a longitudinal axis of the surgical stapler, wherein the first and second stapler halves are configured to pivot relative to each other about the proximal pivot projection; and
   (d) a slide releasably coupled to the other of the first or second stapler halves, wherein the slide is configured to translate longitudinally between a distal locked state in which the slide selectively captures the proximal pivot projection and a proximal unlocked state in which the slide selectively releases the proximal pivot projection, wherein the slide includes an aperture configured to pivotably receive the proximal pivot projection when in the locked state.

2. The surgical stapler of claim 1, wherein the aperture is distally open-ended.

3. The surgical stapler of claim 1, wherein the other of the first or second stapler halves includes at least one proximal notch configured to pivotably receive the proximal pivot projection, wherein the aperture defines an upper peripheral edge configured to rotatably sandwich the proximal pivot projection against a closed end of the at least one proximal notch when in the locked state.

4. The surgical stapler of claim 1, wherein the slide includes at least one first coupling member, wherein the other of the first or second stapler halves includes at least one second coupling member configured to selectively engage the at least one first coupling member when the slide is in at least one of the unlocked or locked states.

5. The surgical stapler of claim 4, wherein the at least one second coupling member includes:
   (i) a proximal second coupling member configured to selectively engage the at least one first coupling member when the slide is in the unlocked state, and
   (ii) a distal second coupling member configured to selectively engage the at least one first coupling member when the slide is in the locked state.

6. The surgical stapler of claim 4, wherein the at least one second coupling member is configured to selectively engage the at least one first coupling member with at least one of a friction fit or a snap fit when the slide is in at least one of the unlocked or locked states.

7. The surgical stapler of claim 4, wherein each of the at least one first coupling member includes one of a detent member or an indent member, wherein each of the at least one second coupling member includes the other of a detent member or an indent member.

8. The surgical stapler of claim 4, wherein the at least one first coupling member is configured to selectively disengage the at least one second coupling member in response to application of a threshold longitudinal force between the slide and the other of the first or second stapler halves for translating the slide between the unlocked and locked states.

9. The surgical stapler of claim 4, wherein the at least one first coupling member includes at least one laterally opposed pair of first coupling members, wherein the at least one second coupling member includes at least one laterally opposed pair of second coupling members.

10. The surgical stapler of claim 1, wherein the slide is configured to continuously capture the proximal pivot projection while in the locked state during pivoting of the first stapler half relative to the second stapler half about the proximal pivot projection between a clamped state of the surgical stapler and an open state of the surgical stapler in which proximal ends of the first and second stapler halves remain releasably coupled together.

11. The surgical stapler of claim 1, wherein the proximal pivot projection is positioned on the second stapler half and the slide is positioned on the first stapler half.

12. The surgical stapler of claim 1, wherein the proximal pivot projection is positioned on the first stapler half and the slide is positioned on the second stapler half.

13. The surgical stapler of claim 1, wherein the proximal pivot projection includes a pin having a non-circular transverse cross-section.

14. The surgical stapler of claim 13, wherein the pin is generally pear-shaped.

15. The surgical stapler of claim 1, wherein the second stapler half includes an elongate member having a distal portion configured to receive a staple cartridge.

16. A surgical stapler comprising:
   (a) a first stapler half including an anvil surface having a plurality of staple forming pockets;
   (b) a second stapler half configured to releasably couple with the first stapler half, wherein the second stapler half is operable to deploy staples toward the anvil surface;
   (c) a proximal pivot projection positioned on one of the first or second stapler halves and extending laterally relative to a longitudinal axis of the surgical stapler, wherein the first and second stapler halves are configured to pivot relative to each other about the proximal pivot projection; and
   (d) a slide movably positioned on an exterior of the other of the first or second stapler halves, wherein the slide is configured to translate longitudinally between a distal locked state in which the slide selectively captures the proximal pivot projection and a proximal unlocked state in which the slide selectively releases the proximal pivot projection, wherein the slide includes an aperture configured to pivotably receive the proximal pivot projection when in the locked state.

17. The surgical stapler of claim 16, wherein the aperture is distally open-ended.

18. A surgical stapler comprising:
   (a) a first stapler half comprising:
      (i) an anvil surface having a plurality of staple forming pockets, and
      (ii) a proximal pivot projection extending laterally relative to a longitudinal axis of the surgical stapler; and
   (b) a second stapler half configured to releasably couple with the first stapler half and to pivot relative thereto about the proximal pivot projection, wherein the second stapler half comprises:
      (i) an elongate member having a distal portion operable to deploy staples toward the anvil surface and at least one proximal notch configured to pivotably receive the proximal pivot projection of the first stapler half, and (ii) a slide configured to translate longitudinally between a distal locked state in which the slide selectively captures the proximal pivot projection and a proximal unlocked state in which the slide selectively releases the proximal pivot projection for coupling and separating the first and second stapler halves, respectively, wherein the slide includes:
  (A) an edge configured to rotatably sandwich the proximal pivot projection against a closed end of the at least one proximal notch when in the locked state, and
  (B) at least one of a detent member or an indent member, wherein the at least one of a detent member or an indent member is configured to secure the slide in at least one of the locked or unlocked states.

19. The surgical stapler of claim 18, wherein the proximal pivot projection has a non-circular transverse cross-section, wherein a portion of the proximal pivot projection is configured to selectively frictionally engage at least one of a proximal surface of the at least one proximal notch or a distally-facing surface of the slide in response to rotation of the first stapler half away from the second stapler half about the proximal pivot projection to an open state in which the first and second stapler halves assume a predetermined maximum angular orientation relative to one another and remain releasably coupled together.

20. The surgical stapler of claim 19, wherein the edge is configured to continuously confront the proximal pivot projection while in the locked state during pivoting of the first stapler half relative to the second stapler half about the proximal pivot projection between a clamped state of the surgical stapler and the open state of the surgical stapler.

* * * * *